(12) United States Patent
Tajima et al.

(10) Patent No.: US 8,445,246 B2
(45) Date of Patent: May 21, 2013

(54) FLAVIN-BINDING GLUCOSE DEHYDROGENASES

(75) Inventors: Ryoko Tajima, Noda (JP); Atsushi Ichiyanagi, Noda (JP); Keiichi Ichikawa, Noda (JP); Taro Yoshimura, Noda (JP)

(73) Assignee: Kikkoman Corporation, Noda-Shi, Chiba (JP)

( * ) Notice: Subject to any disclaimer, the term of this patent is extended or adjusted under 35 U.S.C. 154(b) by 118 days.

(21) Appl. No.: 13/125,315

(22) PCT Filed: Apr. 19, 2010

(86) PCT No.: PCT/JP2010/056899
§ 371 (c)(1),
(2), (4) Date: Apr. 21, 2011

(87) PCT Pub. No.: WO2010/140431
PCT Pub. Date: Dec. 9, 2010

(65) Prior Publication Data
US 2011/0318810 A1 Dec. 29, 2011

(30) Foreign Application Priority Data

Jun. 4, 2009 (JP) ................................. 2009-134623
Nov. 17, 2009 (JP) ................................. 2009-261686

(51) Int. Cl.
*C12N 9/00* (2006.01)
*C12N 15/00* (2006.01)
*C12N 1/20* (2006.01)
*C07H 21/04* (2006.01)

(52) U.S. Cl.
USPC .... 435/183; 435/69.1; 435/252.3; 435/320.1; 536/23.1

(58) Field of Classification Search
USPC ........... 435/183, 320.1, 69.1, 252.3; 536/23.1
See application file for complete search history.

(56) References Cited

U.S. PATENT DOCUMENTS

| | | | |
|---|---|---|---|
| 7,514,250 B2 * | 4/2009 | Omura et al. ................. | 435/189 |
| 2006/0063217 A1 | 3/2006 | Omura et al. | |
| 2008/0003628 A1 | 1/2008 | Kitabayashi et al. | |
| 2008/0220460 A1 | 9/2008 | Kawaminami et al. | |

FOREIGN PATENT DOCUMENTS

| | | |
|---|---|---|
| JP | 2007-289148 A | 11/2007 |
| JP | 2008-154572 A | 7/2008 |
| JP | 2008-237210 A | 10/2008 |
| WO | WO 2004/058958 A1 | 7/2004 |
| WO | WO 2007-139013 A1 | 12/2007 |
| WO | WO 2008/001903 A1 | 1/2008 |
| WO | WO 2008/059777 A1 | 5/2008 |

OTHER PUBLICATIONS

International Search Report dated May 6, 2010 for PCT/JP2010/056899.
Pharmaceutical and Medical Devices Safety Information No. 206, Oct. 2004, Pharmaceutical and Food Safety Bureau, Ministry of Health, Labour and Welfare, pp. 1-17.
Tchan-Gi Bak et al., "Studies on the glucose dehydrogenase of *Aspergillus oryzae*. I. Induction of its synthesis by *p*-benzoquinone and hydroquinone," *Biochim. Biophys. Acta*, 139, pp. 265-276, (1967).
Tchan-Gi Bak at al., "Studies on glucose dehydrogenase of *Aspergillus oryzae*. II. Purification and physical and chemical properties," *Biochim. Biophys. Acta*, 139, pp. 277-293, (1967).
Tchan-Gi Bak et al., "Studies on glucose dehydrogenase of *Aspergillus oryzae*. III. General enzymatic properties," *Biochim. Biophys. Acta*, 146, 317-327, (1967).
Tchan-Gi Bak et al., "Studies on glucose dehydrogenase of *Aspergillus oryzae*. IV. Histidyl residue as an active site," *Biochim. Biophys. Acta*, 146, pp. 328-335, (1967).
Current Protocols in Molecular Biology, Wiley Interscience, 1989, Units 4.3 and 4.5.
Jae-Hyuk Yu et al., "Double-joint PCR: a PCR-based molecular tool for gene manipulations in filamentous fungi," *Fungal Genetics and Biology*, 2004, vol. 41, pp. 973-981.

* cited by examiner

*Primary Examiner* — Karen Cochrane Carlson
(74) *Attorney, Agent, or Firm* — Holtz Holtz Goodman & Chick PC

(57) ABSTRACT

A flavin-binding glucose dehydrogenase with a high substrate specificity for D-glucose. The flavin-binding glucose dehydrogenase which is derived from a microorganism belonging to the genus *Mucor*. The flavin-binding glucose dehydrogenase has a low reactivity for maltose, D-galactose and D-xylose compared to its reactivity for D-glucose, and therefore is relatively unaffected by these saccharide compounds. The flavin-binding glucose dehydrogenase is also relatively unaffected by dissolved oxygen, and allows accurate measurement of glucose amounts even in the presence of saccharide compounds other than glucose in samples.

20 Claims, 6 Drawing Sheets

FLAVIN-BINDING GLUCOSE DEHYDROGENASES

CROSS-REFERENCE TO RELATED APPLICATION

This application is a United States national phase application of International Application PCT/JP2010/056899 filed Apr. 19, 2010.

TECHNICAL FIELD

The present invention relates to novel flavin-binding glucose dehydrogenases that use flavin compounds as coenzymes, and to a method for producing the same.

BACKGROUND ART

Blood glucose concentration (blood glucose level) is an important marker for diabetes. Devices for self-monitoring of blood glucose levels by diabetes patients include widely used devices for Self-Monitoring of Blood Glucose (SMBG) that employ electrochemical biosensors. The biosensors used in SMBG devices of the prior art employ enzymes whose substrate is glucose, such as glucose oxidase (GOD). However, because GOD uses oxygen as an electron acceptor, the dissolved oxygen in measuring samples can affect measurement with SMBG devices employing GOD, potentially interfering with precise measurement values.

On the other hand, various glucose dehydrogenases (hereunder, GDH) are known as enzymes whose substrate is glucose but do not use oxygen as an electron acceptor. Specifically, there have been discovered GDH(NAD(P)-GDH) types, which use nicotinamide dinucleotide (NAD) or nicotinamide dinucleotide phosphoric acid (NADP) as coenzymes, and GDH(PQQ-GDH), which uses pyrroloquinoline quinone (PQQ) as a coenzyme, and these are employed in the biosensors of SMBG devices. However, NAD(P)-GDH has poor enzyme stability and requires addition of coenzyme, while PQQ-GDH has low substrate specificity and also acts on saccharide compounds such as maltose, D-galactose and D-xylose in addition to the measurement target glucose, and therefore saccharide compounds other than glucose in the measuring sample can affect the measured value, making it impossible to obtain an accurate measured value.

When blood glucose levels of diabetes patients that have undergone infusion are measured using SMBG devices employing PQQ-GDH as a biosensor, which have come into use in recent years, the PQQ-GDH also acts on maltose in the infusion, yielding a measured value that is higher than the actual blood glucose level, and cases have been reported in which patients have suffered hypoglycemia as a result of intervention based on such values. It has been shown that the same problem can also occur for patients undergoing galactose load testing and xylose absorption testing (see Non-patent document 1, for example). In light of this, the Pharmaceutical and Food Safety Bureau of the Ministry of Health, Labour and Welfare has conducted crossreactive testing, with the aim of examining effects on blood glucose measurement by addition of different saccharides to glucose solutions, and as a result it has been shown that addition of 600 mg/dL of maltose, 300 mg/dL of D-galactose or 200 mg/dL of D-xylose causes the measured value in a blood glucose measuring kit based on PQQ-GDH to be approximately 2.5-3 times higher than the actual glucose level. In other words, it has been determined that maltose. D-galactose and D-xylose potentially present in measuring samples result in inaccurate measured values, and it is therefore highly desirable to develop GDH with high substrate specificity allowing specific measurement of glucose without being affected by saccharide compounds that can cause measurement errors.

In light of this background, research is being conducted on types of GDH that utilize other coenzymes. For example, Non-patent documents 2 to 5 have reported GDH enzymes derived from *Aspergillus oryzae*, although no details are mentioned regarding their substrate specificities. Patent documents 1 to 3 disclose glucose dehydrogenase (FAD-GDH) having *Aspergillus*-derived flavin adenine dinucleotide (FAD) as a coenzyme, and Patent document 4 discloses *Aspergillus*-derived FAD-GDH with reduced activity for D-xylose.

Patent documents 1 to 4 describe FAD-GDH having low reactivity for one or more types of saccharide compounds that are not D-glucose, but no flavin-binding GDH with sufficiently low reactivity for maltose, D-galactose and D-xylose is known. Furthermore, no flavin-binding GDH is known that allows accurate measurement of glucose levels without being affected by the aforementioned saccharide compounds under conditions in which D-glucose, maltose, D-galactose and D-xylose are present.

[Patent document 1] Japanese Unexamined Patent Application Publication No. 2007-289148

[Patent document 2] International Patent Publication No. WO 04/058958

[Patent document 3] International Patent Publication No. WO 07/139,013

[Patent document 4] Japanese Unexamined Patent Application Publication No. 2008-237210

[Non-patent document 1] Pharmaceuticals and Medical Devices Safety Information No. 206, October 2004, Pharmaceutical and Food Safety Bureau of the Ministry of Health, Labour and Welfare

[Non-patent document 2] Studies on the glucose dehydrogenase of *Aspergillus oryzae*. I. Induction of its synthesis by p-benzoquinone and hydroquinone, T. C. Bak, and R. Sato, Biochim. Biophys. Acta, 139, 265-276 (1967)

[Non-patent document 3] Studies on the glucose dehydrogenase of *Aspergillus oryzae*. II. Purification and physical and chemical properties, T. C. Bak, Biochim, Biophys. Acta, 139, 277-293 (1967).

[Non-patent document 4] Studies on the glucose dehydrogenase of *Aspergillus oryzae*. III. General enzymatic properties, T. C. Bak, Biochim. Biophys. Acta, 146, 317-327 (1967).

[Non-patent document 5] Studies on the glucose dehydrogenase of *Aspergillus oryzae*. IV. Histidyl residue as an active site, T. C. Bak, and R. Sato, Biochim Biophys. Acta, 146, 328-335 (1967).

SUMMARY OF INVENTION

Technical Problem

According to the invention there are provided novel GDH enzymes having high specificity for D-glucose, and allowing accurate measurement of D-glucose levels even under conditions in which saccharide compounds other than D-glucose are co-present.

Solution to Problem

The present inventors conducted much diligent research with the aim of solving the problems mentioned above, and as a result of screening for microorganisms that produce novel GDH enzymes allowing accurate measurement of glucose levels, there were discovered novel GDH from strains belonging to the subphylum Mucormycotina, having high specificity for glucose and exhibiting GDH activity allowing accurate measurement of glucose even when the measurement is conducted under conditions in which saccharide compounds other than glucose are co-present. These novel GMT enzymes were purified and their properties determined, and they were confirmed to be novel flavin-binding GDH enzymes, while actual measurement of D-glucose was also conducted in the presence of maltose, D-galactose and D-xylose and the amino acid sequences of the novel GDH enzymes as well as the nucleotide sequences of the genes coding therefor were obtained, whereupon the invention was completed.

Specifically, the present invention provides the following.

(1) A flavin-binding GDH having the following properties (i) to (iii):

(i) Action: It exhibits GDH activity in the presence of an electron acceptor, (ii) Molecular weight: The molecular weight of the polypeptide chain portion of the protein is approximately 80 kDa, (iii) Substrate specificity: It has low reactivity for maltose, D-galactose and D-xylose, with respect to its reactivity for D-glucose.

(2) A flavin-binding GDH according to (1) above, wherein the reactivity for any of maltose, D-galactose and D-xylose is no greater than 2%, where the reactivity for D-glucose is defined as 100%.

(3) A flavin-binding GDH according to (1) or (2) above, wherein the reactivity for D-glucose, when one or more of the following saccharide compounds (a) to (c) are present:

(a) maltose
(b) D-galactose
(c) D-xylose is 96%-104%, where the reactivity for D-glucose in the absence of (a) to (c) is defined as 100%.

(4) A flavin-binding GDH according to any one of (1) to (3) above, which has an optimum pH of 6.5-7.0, an optimum temperature of 37-40° C., a stable pH range of 3.5-7.0 and a residual activity of at least 80% after heat treatment at 40° C. for 15 minutes.

(5) A flavin-binding GDH according to any one of (1) to (4) above, which is derived from a microorganism classified as subphylum Mucormycotina, preferably class Mucoromycetes, more preferably order Mucorales, and even more preferably family Mucoraceae.

(6) A flavin-binding GDH according to (5) above, which is derived from a microorganism classified as genus *Mucor*.

(7) A method for producing a flavin-binding GDH according to any one of (1) to (6) above, wherein a microorganism classified as genus *Mucor* is cultured in culture medium, and flavin-binding GDH is obtained from the microbial cells.

(8) A method for producing a flavin-binding GDH according to (7) above, wherein the microorganism is one or more selected from among *Mucor prainii, Mucor juvanicus* and *Mucor circinelloides* f. *circinelloides*.

(9) A flavin-binding GDH according to any one of (1) to (6) above, which has the amino acid sequence listed as SEQ ID NO: 1 or SEQ ID NO: 3, or an amino acid sequence having at least 80% homology with the amino acid sequence,

(10) A flavin-binding GDH gene comprising DNA selected from the group consisting of the following (A) to (E):

(A) DNA coding for the amino acid sequence listed as SEQ ID NO: 1;

(B) DNA comprising the nucleotide sequence listed as SEQ ID NO: 2;

(C) DNA coding for the amino acid sequence listed as SEQ ID NO: 3;

(D) DNA comprising the nucleotide sequence listed as SEQ ID NO: 4;

(E) DNA having a nucleotide sequence with at least 80% homology with the nucleotide sequence listed as SEQ ID NO: 2 or SEQ ID NO: 4 and coding for a protein having flavin-binding GDH enzyme activity.

(11) Recombinant DNA comprising a flavin-binding GDH gene according to (10) above inserted into vector DNA.

(12) A transformant having recombinant DNA according to (11) above introduced therein.

(13) A method for producing flavin-binding GDH having low reactivity for maltose, D-galactose and D-xylose with respect to its reactivity for D-glucose, wherein a microorganism comprising a flavin-binding GDH gene according to (10) above or recombinant DNA according to (11) above and capable of producing flavin-binding GDH is cultured, and the flavin-binding GDH is obtained from the culture.

Advantageous Effects of Invention

The flavin-binding GDH of the invention allows accurate measurement of D-glucose levels without being affected by saccharide compounds such as maltose, D-galactose and D-xylose present in measuring samples. It is thus possible to obtain accurate blood glucose level measurements even for samples from patients undergoing maltose-containing infusion, or patients undergoing galactose load testing or xylose absorption testing.

Figure 1:
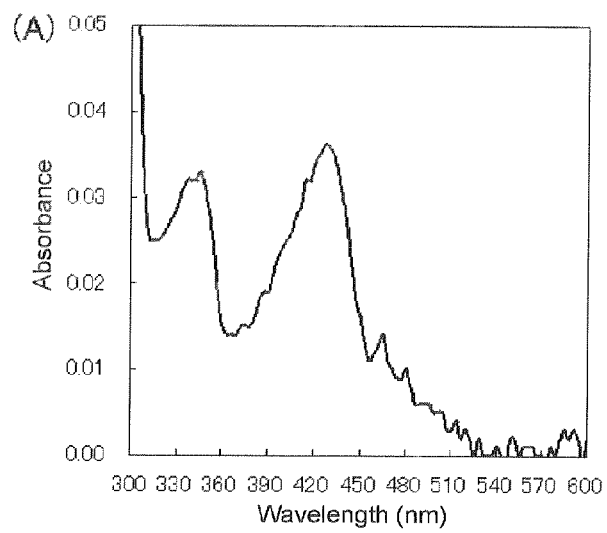
FIG. 1 is a graph showing the absorption spectrum for a flavin-binding GDH of the invention.
Figure 1:
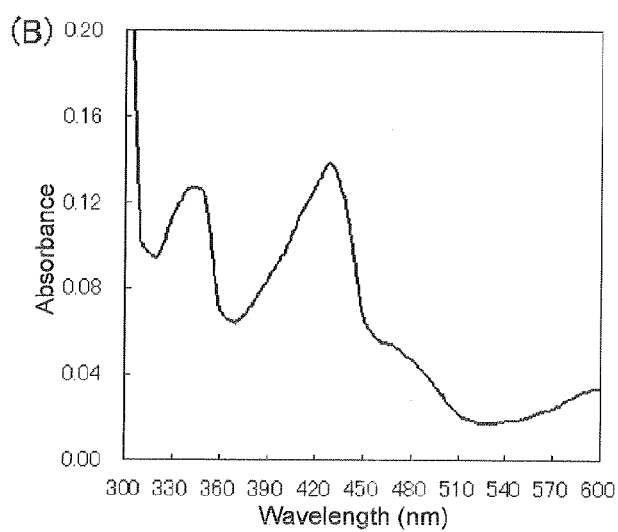
Figure 1:
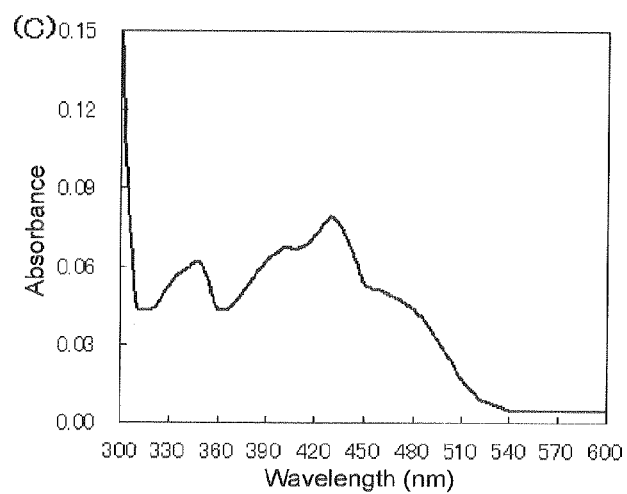

DESCRIPTION OF EMBODIMENTS (Substrate Specificity of Flavin-Binding GDH)

The flavin-binding GDH of the invention has excellent substrate specificity and very high selectivity for D-glucose. Specifically, the flavin-binding GDH of the invention has very low reactivity for maltose, D-galactose and D-xylose. More specifically, the reactivity for any of maltose, D-galactose and D-xylose is no greater than 2%, where the reactivity for D-glucose is defined as 100%. Because the flavin-binding GDH of the invention has such high substrate specificity, it allows accurate measurement of D-glucose levels without being affected by saccharide compounds such as maltose, D-galactose and D-xylose present in measuring samples, even when the samples are from patients undergoing maltose-containing infusion, or patients undergoing galactose load testing or xylose absorption testing.

The flavin-binding GDH of the invention gives extremely low measured values when measurement is conducted using saccharide compounds such as maltose, D-galactose and D-xylose as substrates instead of D-glucose, and permits accurate measurement of glucose values even under conditions where saccharide compounds such as maltose, D-galactose and D-xylose are contaminants. Specifically, the measured value in cases where one or more contaminating saccharide compounds from among maltose, D-galactose and D-xylose are present is 96%-103%, where the reactivity for D-glucose under conditions without the presence of these contaminating saccharide compounds is defined as 100%, and the measured value is 96%-104% even when all of the saccharides maltose, D-galactose and D-xylose are simultaneously present as contaminating saccharide compounds. Using a flavin-binding GDH having such properties allows accurate measurement of glucose levels even in cases where maltose or D-galactose and D-xylose are present in a measuring sample, and is preferred.

(Enzymo-Chemical Properties of Flavin-Binding GDH of the Invention)

Examples of preferred enzymes as flavin-binding GDH enzymes of the invention are those having the following enzymo-chemical properties.
(1) Action: Exhibiting GDH activity in the presence of an electron acceptor.
(2) Molecular weight: The molecular weight of the polypeptide chain portion of the protein is approximately 80 kDa.
(3) Substrate specificity: Having low reactivity for maltose, D-galactose and D-xylose, with respect to reactivity for D-glucose.
(4) Optimum pH: pH 6.5-7.0
(5) Optimum temperature: 37-40° C.
(6) Stable pH range: pH 3.5-7.0
(7) Thermostability: Having residual activity of at least 80% after heat treatment at 40° C. for 15 minutes.
(8) Using a flavin compound as coenzyme.
(9) Km value: Having a Km value of 26-33 mM for D-glucose.

GDH having such enzymo-chemical properties allows accurate measurement of D-glucose levels without being affected by saccharide compounds such as maltose, D-galactose and D-xylose present in measuring samples. Furthermore, because it has satisfactory activity in a pH range and temperature range that are suitable for clinical diagnosis such as measurement of blood glucose levels, it can be suitably used as a diagnostic measurement reagent or the like.

The property parameters mentioned above are typical examples, but these parameters have permissible variable ranges within limits allowing the effect of the invention to be achieved when measurement of D-glucose is conducted under prescribed measuring conditions. For example, the parameters of stable pH range, optimum pH range and optimum temperature range may be slightly wider than the aforementioned typical ranges, within limits that include the prescribed measuring conditions, or conversely, they may have slightly narrower ranges than the typical ranges mentioned, so long as sufficient activity and/or stability are ensured under the measuring conditions. Generally speaking, a smaller Km value corresponds to superior substrate specificity, but the enzyme of the invention may have a value in a range in which sufficient substrate selection is essentially achieved under the prescribed measuring conditions.

The enzymo-chemical properties can be examined using known methods for determining enzyme properties, such as the methods described in the examples described below. The enzyme properties can be examined to some extent in the culture solution of the microorganism that produces the flavin-binding GDH of the invention, or at a stage during the purification step, and more specifically, it can be examined using a purified enzyme.

A purified enzyme is an enzyme separated into a state in which it contains substantially no components other than the enzyme, and especially no proteins other than the enzyme (contaminant proteins). Specifically, the contaminant protein content is less than about 20%, preferably less than about 10%, more preferably less than about 5% and even more preferably less than about 1% of the total, based on the weight. The terms "MpGDH", "MjGDH" and "McGDH" used later throughout the present specification refer to purified enzymes, unless otherwise specified.

The electron acceptor utilized by the flavin-binding GDH of the invention is not particularly restricted, and for example, any electron acceptor may be used which is known as a reagent component suitable for use in blood glucose level measurement.

The coenzyme used by the flavin-binding GDH of the invention is a flavin compound. Flavin compounds include flavin adenine dinucleotide (FAD) and flavin mononucleotide (FMN).

Examples of preferred enzymes as the flavin-binding GDH of the invention include flavin-binding GDH enzymes wherein the molecular weight of the polypeptide chain portion of the protein is approximately 80 kDa, as measured by SDS-polyacrylamide electrophoresis. The flavin-binding GDH of the invention is assumed to have bonded sugar chains, and without a procedure for removing the sugar chains, the molecular weight determined by SDS-polyacrylamide electrophoresis will tend to be measured as slightly higher.

Examples of preferred enzymes as the flavin-binding GDH of the invention include flavin-binding GDH enzymes having Km values of 26-33 mM for D-glucose.

(Principle of Action and Activity Measurement Method for Flavin-Binding GDH)

The flavin-binding GDH of the invention catalyzes a reaction in which a hydroxyl group of glucose is oxidized in the presence of an electron acceptor, to produce glucono-δ-lactone.

This principle can therefore be used for measurement of the activity of a flavin-binding GDH of the invention, in the following measuring system employing, for example, phenazine methosulfate (PMS) and 2,6-dichloroindophenol (DCIP) as electron acceptors.

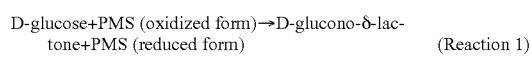

D-glucose+PMS (oxidized form)→D-glucono-δ-lactone+PMS (reduced form)     (Reaction 1)

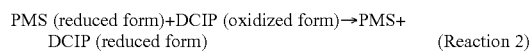

PMS (reduced form)+DCIP (oxidized form)→PMS+DCIP (reduced form)     (Reaction 2)

First, in (Reaction 1), PMS (reduced form) is produced as glucose is oxidized. In the subsequent (Reaction 2), DCIP is reduced as PMS is oxidized, and therefore loss of the oxidized form of DCIP can be measured from the change in absorbance of the 600 nm wavelength.

Specifically, the activity of the flavin-binding GDH is measured in the following manner, according to the invention. A mixture of 1.79 mL of 100 mM phosphate buffer (pH 7.0), 0.08 mL of a 1.25 M D-glucose solution and 0.01 mL of a 20 mM DCIP solution is warmed at 37° C. for 5 minutes. Next, 0.02 mL of a 20 mM PMS solution and 0.1 mL of an enzyme sample solution are added, and reaction is initiated. The absorbance is measured at the start of the reaction and periodically thereafter, the reduction in absorbance at 600 nm per minute (ΔA600) as the enzyme reaction proceeds is determined, and the flavin-binding GDH activity is calculated by the following formula. Here, 1 U of flavin-binding GDH activity is defined as the amount of enzyme that reduces 1 µmol of DCIP in 1 minute in the presence of D-glucose at 50 mM concentration at 37° C.

$$\text{GDH activity}(U/\text{mL}) = \frac{-(\Delta A600 - \Delta A600_{blank}) \times 2.0 \times df}{16.3 \times 0.1 \times 1.0} \quad \text{[Formula 1]}$$

The value of 2.0 in the formula is the liquid volume (mL) of reaction reagent+enzyme reagent, 16.3 is the millimolar molecular absorption coefficient (cm$^2$/µmol) under the activity measuring conditions, 0.1 is the liquid volume (mL) of the enzyme solution, 1.0 is the optical path length (cm) of the cell, $\Delta A600_{blank}$ is the reduction in absorbance at 600 nm per minute, when the reaction is initiated by addition of 10 mM acetate buffer instead of the enzyme sample solution, and df represents the degree of dilution.

(Source of Flavin-Binding GDH)

The flavin-binding GDH of the invention having the properties described above can be obtained from a microorganism classified as subphylum Mucormycotina, preferably class Mucoromycetes, more preferably order Mucorales, and even more preferably family Mucoraceae. Examples of microorganisms classified as subphylum Mucormycotina, preferably class Mucoromycetes, more preferably order Mucorales and even more preferably family Mucoraceae, include the genera *Mucor, Absidia* and *Actinomucor*. Specific examples of preferred microorganisms classified in the genus *Mucor* and producing flavin-binding GDH according to the invention include *Mucor prainii, Mucor javanicus* and *Mucor circinelloides f. circinelloides*. More specifically, there may be mentioned *Mucor prainii* NISI0103, *Mucor javanicus* NISI0111 and *Mucor circinelloides f. circinelloides* NISL0117. Specific examples of preferred microorganisms classified in the genus *Absidia* and producing flavin-binding GDH according to the invention include *Absidia cylindrospora* and *Absidia hyalospora*. More specifically, there may be mentioned *Absidia cylindrospora* NISL0211 and *Absidia hyalospora* NISL0218. Specific examples of preferred microorganisms classified in the genus *Actinomucor* and producing flavin-binding GDH according to the invention include *Actinomucor elegans*. More specifically, there may be mentioned *Actinomucor elegans* NISL9082. These strains have been deposited at the NISL (Noda Industrial Science Laboratory), and may be obtained through a prescribed procedure.

As mentioned above, the flavin-binding GDH of the invention is "a flavin-binding GDH derived from a microorganism classified as subphylum Mucormycotina, preferably class Mucoromycetes, more preferably order Mucorales, and even more preferably family Mucoraceae, and having the properties described above". Moreover, "a flavin-binding GDH derived from a microorganism classified as subphylum Mucormycotina, preferably class Mucoromycetes, more preferably order Mucorales, and even more preferably family Mucoraceae, and having the properties described above" also encompasses any recombinant flavin-binding GDH enzyme produced using a gene coding for a flavin-binding GDH enzyme obtained from any of these flavin-binding GDH-producing microorganisms by known genetic engineering methods, with partial modification if necessary, and transferring the gene into an appropriate host microorganism by a known method. Similarly, the invention also encompasses any flavin-binding GDH listed with "microorganism classified in the genus *Mucor*", or with the name of a specific producing microorganism, if the flavin-binding GDH is obtained based on the relevant genetic information from each and has the aforementioned properties.

(Amino Acid Sequence of Flavin-Binding GDH)

The flavin-binding GDH of the invention has the amino acid sequence listed as SEQ ID NO: 1 or SEQ ID NO: 3, or an amino acid sequence having at least 80% homology with the amino acid sequence, or an amino acid sequence which is any of the aforementioned amino acid sequences having a deletion, substitution or addition of one or more amino acids. Flavin-binding GDH having the amino acid sequence listed as SEQ ID NO: 1 or SEQ ID NO: 3 has the properties described above. Also encompassed within the flavin-binding GDH of the invention are GDH enzymes having amino acid sequences with at least 80% homology, and preferably 85%, more preferably 90% and most preferably 95% or greater homology, with the amino acid sequence listed as SEQ ID NO: 1 or SEQ ID NO: 3, and exhibiting the same properties as flavin-binding GDH having the amino acid sequence listed as SEQ ID NO: 1 or SEQ ID NO: 3.

(Sequence of Gene Coding for Flavin-Binding GDH)

A gene coding for the flavin-binding GDH of the invention is DNA coding for flavin-binding GDH having the amino acid sequence listed as SEQ ID NO: 1 or SEQ ID NO: 3, or an amino acid sequence having at least 80% homology with the amino acid sequence, or an amino acid sequence which is any of the aforementioned amino acid sequences having a deletion, substitution or addition of one or more amino acids. A gene coding for the flavin-binding GDH of the invention may also be DNA comprising the nucleotide sequence listed as SEQ ID NO: 2 or SEQ ID NO: 4. Alternatively, a gene coding for the flavin-binding GDH of the invention may be DNA having a nucleotide sequence with at least 80% homology, preferably 85%, more preferably 90% and most preferably 95% or greater homology with the nucleotide sequence listed as SEQ ID NO: 2 or SEQ ID NO: 4, and coding for a protein with flavin-binding GDH enzyme activity.

(Vector Comprising Gene Sequence Coding for Flavin-Binding GDH, and Transformants)

A gene coding for the flavin-binding GDH of the invention may be inserted into an appropriate known vector. The vector may be transferred into an appropriate known host to create transformants in which recombinant DNA comprising the flavin-binding GDH gene has been transferred. Methods for obtaining such genes, methods for obtaining gene sequence and amino acid sequence information, methods for producing vectors and methods for creating transformants are known to those skilled in the art, and an example will be described hereunder.

A commonly employed gene cloning method may be used to obtain a flavin-binding GDH gene from a microorganism producing flavin-binding GDH. For example, chromosomal DNA or mRNA may be extracted from microbial cells or other types of cells having the ability to produce flavin-binding GDH, by the method described in Current Protocols in Molecular Biology (WILEY Interscience, 1989), for example. Also, mRNA may be used as a template for synthesis of cDNA. The chromosomal DNA or cDNA obtained in this manner may be used to construct a chromosomal DNA or cDNA library.

Next, suitable probe DNA may be synthesized based on the amino acid sequence of the flavin-binding GDH, and used for screening from the chromosomal DNA or cDNA library, or alternatively, appropriate primer DNA may be prepared based on the amino acid sequence, and suitable Polymerase Chain Reaction (PCR) such as 5' RACE or 3' RACE conducted to amplify DNA comprising fragments of the gene of interest, which are then linked to obtain DNA comprising the full-length gene of interest.

Preferred examples of genes coding for flavin-binding GDH obtained in this manner are flavin-binding GDH genes derived from the genus *Mucor*. For convenience, these genes are preferably linked in different vectors by a common method, and for example, they may be obtained by preparing a recombinant plasmid comprising an isolated gene coding for a *Mucor*-derived flavin-binding GDH, and using, for example, QIAGEN (product of Qiagen Inc.) for extraction and purification. The vector DNA used for the invention may be, for example, plasmid vector DNA, bacteriophage vector DNA, or the like. A specific preferred example is pBluescript-II SK+ (Stratagene).

Determination and confirmation of the nucleotide sequence of the flavin-binding GDH gene obtained by the method described above can be accomplished using, for example, a CEQ2000 Multi-Capillary DNA Analysis System (product of Beckman Coulter, Inc.).

The flavin-binding GDH gene obtained in this manner may be incorporated by a common method into a vector such as a bacteriophage, cosmid, or a plasmid used for transformation of prokaryotic cells or eukaryotic cells, for transformation or transfection of the corresponding host of the vector by a common method. The host may be, for example, a microorganism belonging to the genus *Escherichia*, such as *E. coli* K-12, and preferably *E. coli* JM109 or DH5α (both by Takara Bio, Inc.), and these hosts may be transformed or transfected to obtain the respective strains. Culturing of the transformants obtained in this manner allows large-volume production of flavin-binding GDH.

(Production of Flavin-Binding GDH)

The flavin-binding GDH of the invention can be produced using any known enzyme-producing method. For example, the flavin-binding GDH-producing microorganism may be cultured in medium to produce the target flavin-binding GDH, and the enzyme may be obtained from the culture or from inside the cultured cells. Also, a microorganism incorporating either the flavin-binding GDH gene of the invention or recombinant DNA containing the GDH gene, and having the capability to produce flavin-binding GDH may be cultured, and the flavin-binding glucose dehydrogenase obtained form the culture.

Culturing of the microorganism may be accomplished by a common solid culturing method, but if possible it is preferably accomplished by employing a liquid culturing method. The medium used for the culturing may contain a carbon source, nitrogen source, inorganic materials and other nutrients as appropriate, and may be a synthetic culture medium or natural culture medium, and any medium that allows efficient production of the enzyme of interest.

The carbon source used for the culture medium may be any carbon compound that can be assimilated, with examples including glucose, starch hydrolysate, glycerin, fructose and molasses. The nitrogen source may be any nitrogen compound that can be utilized, with examples including yeast extract, peptone, meat extract, corn steep liquor, soybean flour, malt extract, amino acid, ammonium sulfate and ammonium nitrate. Examples of inorganic materials include various salts such as table salt, potassium chloride, magnesium sulfate, manganese chloride, ferrous sulfite, monopotassium phosphate, dipotassium phosphate, sodium carbonate and calcium chloride. Vitamins, antifoaming agents and the like may also be added as necessary.

In addition, nutrients or other components that can improve production volume of the flavin-binding GDH of the invention by their addition may also be used, either alone or in combinations.

The culturing conditions will differ depending on the microorganism to be cultured. For example, the initial pH of the culture medium may be adjusted to pH 5-10, the culturing temperature to 20-40° C. and the culturing time appropriately set to 10-50 hours, 15-25 hours or 1-2 days, and aerated agitated submerged culture, shaking culture or static culture. As an example of culture medium and culturing conditions for culturing of a microorganism of subphylum Mucormycotina, there may be mentioned shaking for 2 days at 30° C., 130 rpm, using culture medium at pH 6.0 comprising 2.0% yeast extract and 4% glucose. As an example of culture medium and culturing conditions for culturing of a microorganism such as *E. coli*, there may be mentioned shaking culture for 4 days at 25° C., 120 rpm, using culture medium at pH 7.3 comprising 0.1% yeast extract, 0.1% malt extract, 0.1% potassium dihydrogenphosphate and 0.05% magnesium sulfate.

Upon completion of culturing of the enzyme-producing microorganism, common enzyme extraction means may be employed to extract the flavin-binding GDH to be used in the method of the invention, from the culture or from within the cultured cells. When the enzyme is present in the cells, preferably the cells are separated from the culture by a procedure such as filtration or centrifugal separation, and the enzyme extracted from the cells. Various methods may be employed either alone or in combinations, such as a method of using common cell-disrupting means such as an ultrasonic disruptor, French press, Dyno-Mill or the like to disrupt the cells, a method of lysing the cell walls using a cell-wall digesting enzyme such as lysozyme, or a method of using a surfactant such as Triton X-100 to extract the enzyme from the cells.

The insoluble portion may then be removed by filtration or centrifugal separation to obtain an enzyme extract. The flavin-binding GDH is then isolated and purified from the obtained extract as necessary, and after removing the nucleic acid if necessary, ammonium sulfate, alcohol, acetone or the like is added thereto, fractionation is performed, and the precipitate is collected. In order to obtain a highly-purified enzyme preparation, an appropriate method may be selected, such as a gel filtration method using Sephadex, Ultragel, Bio-Gel or the like, an adsorption elution method using an ion exchanger, hydroxyapatite or the like, an affinity chromatography method, or a fractionation method using a molecular sieving membrane or hollow fiber membrane.

The flavin-binding GDH used for measurement according to the invention can be produced in mass using a known gene recombination method. For example, the gene sequences and amino acid sequences of the different flavin-binding GDH enzymes may be analyzed by known methods, and flavin-binding GDH enzymes having the same structures and properties produced in mass in different host microorganisms, based on that information. Also, various known techniques may be used for modification by deletion, substitution, addition and/or insertion of a portion of the gene sequence and amino acid sequence of the flavin-binding GDH, to produce flavin-binding GDH imparted with desired properties.

Since the flavin-binding GDH of the invention, produced in the manner described above, allows accurate measurement of glucose levels even in the presence of contaminating saccharide compounds, it can be satisfactorily applied and implemented in glucose sensors and the like.

The present invention will now be explained in greater detail by examples. However, it is to be understood that the technical scope of the invention is not limited in any way by these examples.

Example 1

Obtaining Flavin-Binding GDH of the Invention

1. Screening of GDH-Producing Cells

GDH-producing cells were screened from among strains separated from the natural environment and approximately 500 stored strains allotted from a culture collection institution (Noda Industrial Science Laboratory). Each test strain was seeded in 3 ml of malt extract culture medium (2.0% malt extract, 2.0% D-glucose, 0.1% polypeptone, pH 6.0), and shake cultured for 3-5 days at 30° C. The culture solution was centrifuged at 800×g for 10 minutes, and the cells were obtained as a precipitate. The cells were then suspended in 10 mM acetate buffer (pH 5.0) and mashed in a Multi-Beads Shocker (product of Yasui Kikai Corp.) (2,000 rpm, 60 seconds, 16 times), and then centrifuged at 4° C., 20,000×g for 10 minutes, and the recovered supernatant was used as a crude enzyme solution.

2. Confirmation of GDH Activity

Each solution was combined by the procedure described below, and the absorbance was measured to determine the GDH activity of the crude enzyme solution. After then mixing 1.79 mL of 100 mM phosphate buffer (pH 7.0), 0.08 mL of a 1.25 M D-glucose solution and 0.01 mL of a 20 mM DCIP solution and warming the mixture at 37° C. for 5 minutes, 0.02 mL of a 20 mM PMS solution and 0.1 mL of an enzyme sample solution were added and reaction was initiated. The reduction in absorbance at 600 nm per minute ($\Delta A600$) from the start of the reaction was measured as the enzyme reaction proceeded, and the GDH activity was calculated by the formula shown below. Here, 1 U of GDH activity was defined as the amount of enzyme that reduced 1 μmol of DCIP in 1 minute in the presence of D-glucose at 50 mM concentration at 37° C.

$$GDH\ activity(U/mL) = \frac{-(\Delta A600 - \Delta A600_{blank}) \times 2.0 \times df}{16.3 \times 0.1 \times 1.0}$$ [Formula 2]

The value of 2.0 in the formula is the liquid volume (mL) of reaction reagent+enzyme reagent, 16.3 is the millimolar molecular absorption coefficient ($cm^2/\mu mol$) under the activity measuring conditions, 0.1 is the liquid volume (mL) of the enzyme solution, 1.0 is the optical path length (cm) of the cell, $\Delta A600_{blank}$ is the reduction in absorbance at 600 nm per minute, when the reaction is initiated by addition of 10 mM acetate buffer instead of the enzyme sample solution, and df represents the degree of dilution.

The results of determining GDH activity in the crude enzyme solution of each strain based on the activity measurement described above are shown in Table 1.

TABLE 1

| GDH activity detected in crude enzyme solutions | |
|---|---|
| Strain name | Activity (U/mL) |
| *Mucor prainii* NISL0103 | 0.187 |
| *Mucor javanicus* NISL0107 | 0.476 |
| *Mucor javanicus* NISL0108 | 0.023 |

TABLE 1-continued

| GDH activity detected in crude enzyme solutions | |
|---|---|
| Strain name | Activity (U/mL) |
| *Mucor javanicus* NISL0111 | 0.714 |
| *Mucor javanicus* NISL0112 | 0.282 |
| *Mucor javanicus* NISL0115 | 0.116 |
| *Mucor circinelloides* f. *circinelloides* NISL0116 | 0.033 |
| *Mucor circinelloides* f. *circinelloides* NISL0117 | 0.136 |
| *Mucor hiemalis* f. *silvaticus* NISL0118 | 0.001 |
| *Absidia cylindrospora* NISL0211 | 0.007 |
| *Absidia hyalospora* NISL0218 | 0.006 |
| *Actinomucor elegans* NISL9082 | 0.012 |

As a result, GDH activity was detected in the crude enzyme solutions derived from *Mucor prainii* NISL0103, *Mucor javanicus* NISL0107, *Mucor javanicus* NISL0108, *Mucor javanicus* NISL0111, *Mucor javanicus* NISL0112, *Mucor javanicus* NISL0115, *Mucor circinelloides* f. *circinelloides* NISL0116, *Mucor circinelloides* f. *circinelloides* NISL0117, *Mucor hiemalis* f. *silvaticus* NISL0118, *Absidia cylindrospora* NISL0211, *Absidia hyalospora* NISL0218 and *Actinomucor elegans* NISL9082.

Example 2

Purification of Flavin-Binding GDH from Genus *Mucor*

After placing 0.1 L of culturing medium (2.0% yeast extract 4% glucose, pH 60) in a 0.5 L volume Sakaguchi flask, *Mucor prainii* NISL0103, *Mucor javanicus* NISL0111 and *Mucor circinelloides* f. *circinelloides* NISL0117 pre-cultured on plate culture medium were seeded therein to approximately 1 $cm^2$ portions and subjected to rotary shake culture for 2 days at 30° C., 130 rpm. These were used as seed cultures, and seeded at 0.2 L each into 20 L of the aforementioned culture medium placed in 30 L-volume jar fermenters (2 jar fermenters) and cultured for 3 days at 30° C., 200 rpm, 0.5 vvm. Upon completion of the culturing, 40 L of culture solution was filtered with a filter cloth and the cells were recovered. The obtained cells were then suspended in 10 mM acetate buffer (pH 5.0).

The cell suspension was conveyed into a Dyno-Mill (150 ml/min) for mashing and then centrifuged at 6,000 g for 30 minutes, and the supernatant was recovered. The supernatant was concentrated using an AIP2013 hollow fiber membrane with a molecular cutoff of 6,000 (product of Asahi Kasei Chemicals Corp.), and then ammonium sulfate was gradually added to the concentrated enzyme solution to 70% saturation, for precipitation of the excess protein. After standing overnight at 4° C., the supernatant was recovered by centrifugal separation (200,000×g, 60 min).

The supernatant was passed through a Toyopearl-Butyl 650C (product of Tosoh Corp.) column (26ϕ×28.5 cm) that had been equilibrated with buffer A (10 mM acetate buffer, 2 M ammonium sulfate, pH 5.0), and eluted by a linear gradient from buffer A to buffer B (10 mM acetate buffer, pH 5.0). The eluted active fraction was concentrated with Centricon Plus-70 (product of Millipore) and then dialyzed against buffer C (10 mM acetate buffer, pH 4.5), passed through a SP Sepharose FastFlow (product of GE Healthcare) column (26ϕ×28.5 cm) that had been equilibrated with buffer C, and eluted with a linear gradient from buffer C to buffer D (10 mM acetate buffer, 200 mM potassium chloride, pH 4.5). The eluted active fraction was concentrated to obtain the purified enzyme. Thereafter, the purified enzymes were denoted as follows: *Mucor prainii* NISL0103-derived GDH as MpGDH, *Mucor javanicus* NISL0111-derived GDH as MjGDH, and *Mucor circinelloides f. circinelloides* NISL0117-derived GDH as McGDH.

Example 3

Examination of Enzymo-Chemical Properties of *Mucor*-Derived Flavin-Binding GDH Enzymes The properties of the purified GDH enzymes obtained in Example 2 were examined.
(a) Absorption Spectrum Measurement
MpGDH, MjGDH and McGDH were dialyzed against 10 mM acetate buffer (pH 5.0), and their absorption spectra at 250-800 nm were measured with a spectrophotometer U-3010 (product of Hitachi High-Technologies Corp.). The measurement results are shown in FIG. 1 (FIG. 1(A) is the absorption spectrum for MpGDH, FIG. 1(B) is the absorption spectrum for MjGDH, and FIG. 1(C) is the absorption spectrum for McGDH). All of the GDH enzymes were confirmed to have two peaks exhibiting maxima near a wavelength of 340-350 nm and a wavelength of 420-430 nm, and since this absorption spectral shape is characteristic of flavin enzymes, the results strongly suggested that the GDH enzymes of the invention are flavin-binding proteins.
(b) Measurement of GOD Activity
The GDH activity and GOD activity were measured using the MpGDH, MjGDH and McGDH obtained in Example 2 and commercially available glucose oxidase derived from *Aspergillus niger* (GOD, product of Biozyme Laboratories). The results are shown in Table 2.

The GDH activity was measured according to the method of Example 1, and GOD activity was measured by the following method using 4-aminoantipyrine (4-AA) and N-ethyl-N-(2-hydroxy-3-sulfopropyl)-3-methylaniline (TOOS). After mixing 30.0 mL of 100 mM phosphate buffer (pH 7.0), 6.0 mL of an 833 mM D-glucose solution, 0.3 mL of a 25 mM 4-AA solution, 0.3 mL of a 40 mM TOOS solution and 0.3 mL of a 500 U/mL, POD solution, 3.0 mL of the mixture was transferred to a test tube and warmed at 37° C. for 5 minutes, after which 0.1 mL of enzyme sample solution was added and reaction was initiated. The increase in absorbance at 555 nm per minute ($\Delta A555$) was measured as the enzyme reaction proceeded, and the GOD activity was calculated by the formula shown below. Here, 1 U of GOD activity was defined as the amount of enzyme that produced 1 μmol of $H_2O_2$ in 1 minute in the presence of D-glucose at 131 mM concentration at 37° C.

$$GOD\ activity(U/mL) = \frac{(\Delta A555 - \Delta A555_{blank}) \times 3.1 \times df}{32.8 \times 0.5 \times 0.1 \times 1.0}$$ [Formula 3]

The value of 3.1 in the formula is the liquid volume (mL) of reaction reagents+enzyme reagent, 32.8 is the millimolar molecular absorption coefficient ($cm^2/\mu mol$) under the activity measuring conditions, 0.5 is the number of molecules of quinoneimine dye produced when 1 molecule of $H_2O_2$ is reduced, 0.1 is the liquid volume (mL) of the enzyme solution, 1.0 is the optical path length (cm) of the cell, $\Delta A555_{blank}$ is the increase in absorbance at 555 nm per minute, when the reaction is initiated by addition of 10 mM acetate buffer instead of the enzyme sample solution, and df represents the degree of dilution.

TABLE 2

Comparison of GDH activity and GOD activity of different enzymes

|  | GDH activity | GOD activity |
|---|---|---|
| MpGDH | 8.80 U/mL | 0.00 U/mL |
| MjGDH | 9.90 U/mL | 0.00 U/mL |
| McGDH | 9.42 U/mL | 0.00 U/mL |
| *Aspergillus niger*-derived GOD | 3.50 U/mL | 9.38 U/mL |

Figure 2:
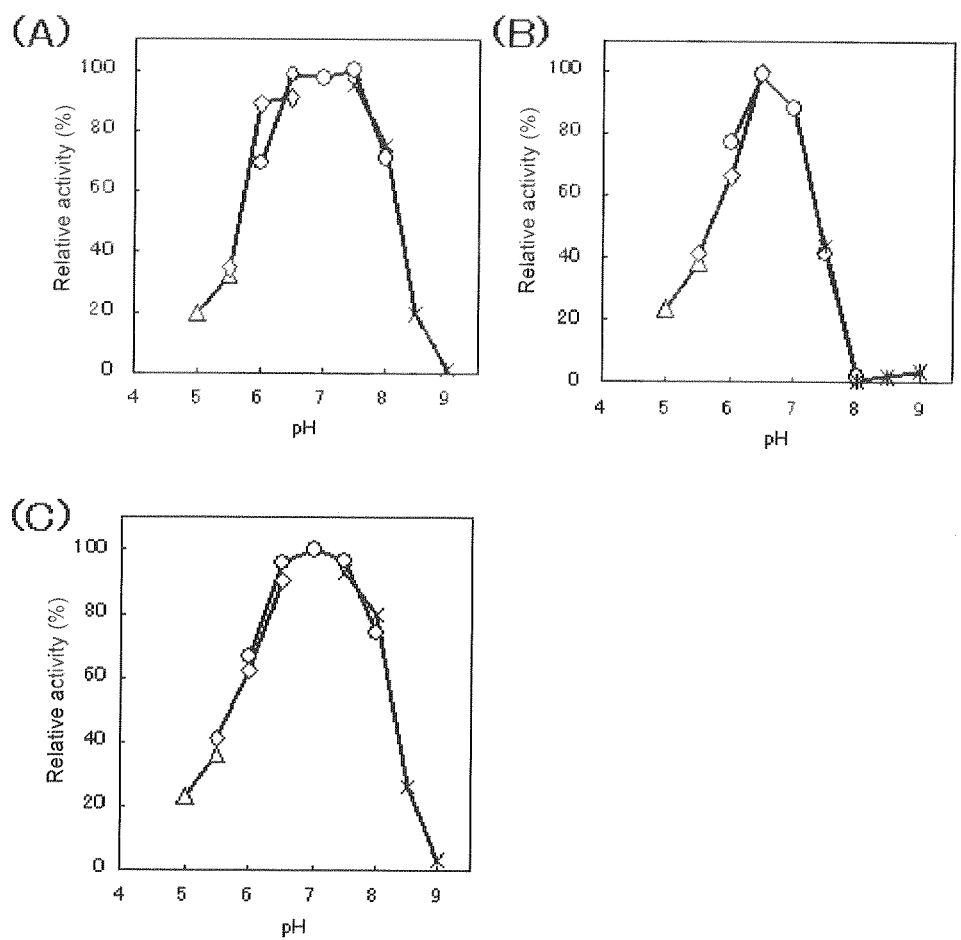
FIG. 2 is a graph showing the optimum pH for a flavin-binding GDH of the invention.
Figure 3:
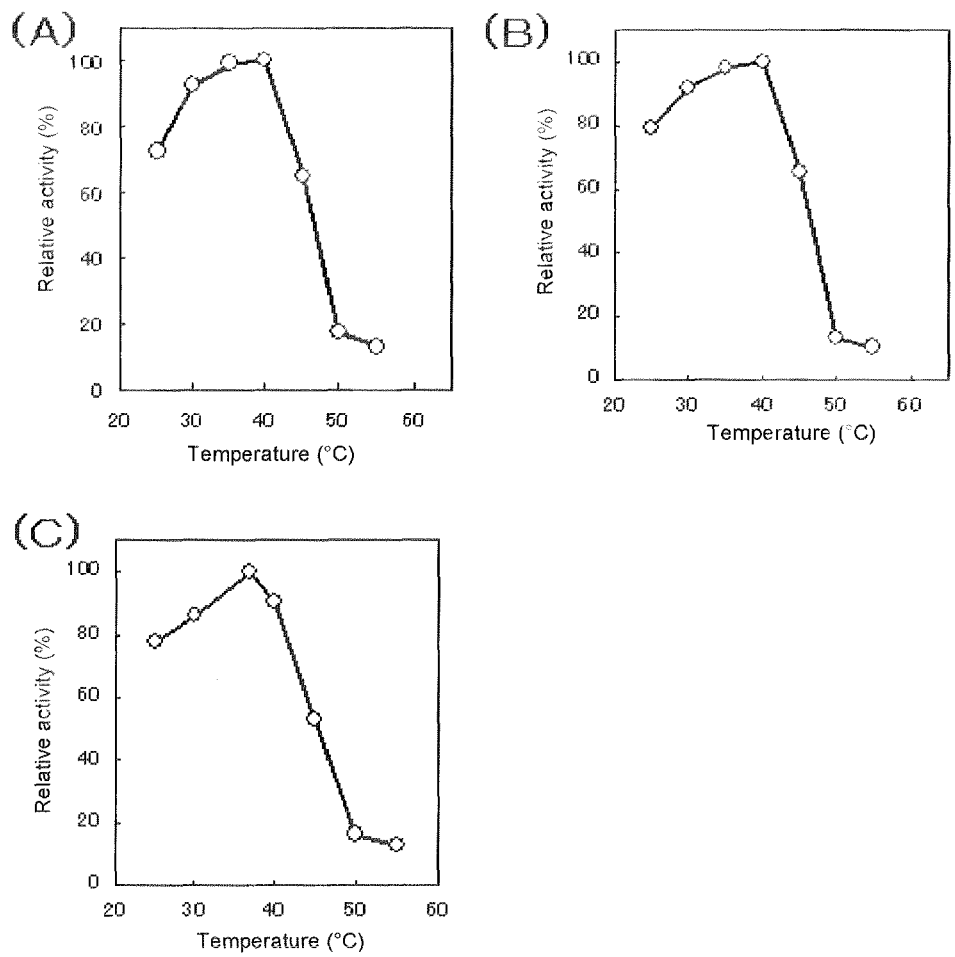
FIG. 3 is a graph showing the optimum temperature for a flavin-binding GDH of the invention.

(c) Optimum pH
The optimum pH for the flavin-binding GDH of the invention was investigated. The results are shown in FIG. 2 (FIG. 2(A) is for MpGDH, (B) is for MjGDH and (C) is for McGDH). Specifically, 100 mM potassium acetate buffer (pH 5.0-5.5 plotted as Δ in the graphs), 100 mM MES-NaOH buffer (pH 5.5-65, plotted as diamonds in the graphs), 100 mM potassium phosphate buffer (pH 6.0-8.0, plotted as circles in the graphs) and 100 mM Tris-HCl buffer (pH 7.5-9.0, plotted as a in the graphs) were used for enzyme reaction at 37° C. at each pH, and the relative activities were compared.
As a result, all of the flavin-binding GDH enzymes exhibited highest activity at pH 6.5 or pH 7.0, with optimum pH values near pH 7.0. Considered separately, the relative activities of MpGDH and McGDH were highest at pH 7.0, and since their maximum relative activities in the surrounding range of pH 6.5-7.5 were 80% or greater, they were considered suitable for use in that range. Also, the relative activity of MjGDH was highest at pH 6.5, and since its maximum relative activity in the surrounding range of pH 6.0-7.0 was 80% or greater, it was considered suitable for use in that range.
(d) Optimum Temperature Range
The activity of the enzyme was measured at different temperatures, based on the activity measuring method described in Example 2. Specifically, 30.0 mL of 100 mM phosphate buffer (pH 7.0). 6.0 mL of an 833 mM D-glucose solution, 0.3 mL of a 25 mM 4-AA solution, 0.3 mL of a 40 mM TOOS solution and 0.3 mL of a 500 U/mL POD solution were mixed and 3.0 mL of the mixture was transferred to a test tube and warmed for 5 minutes at different temperatures instead of warming at 37° C., after which 0.02 mL of 20 mM PMS solution and 0.1 mL of enzyme sample solution were added and reaction was initiated at different temperatures. The absorbance was measured at the start of the reaction and 2 minutes thereafter, and the reduction in absorbance at 600 nm per minute was measured as the enzyme reaction proceeded. The results are shown in FIG. 3 (FIG. 3(A) is for MpGDH, (B) is for MjGDH and (C) is for McGDH). All exhibited maximum activity near 37° C., and the temperature range in which at least 80% of the maximum activity was exhibited was 30-40° C. This suggested that the optimum temperature range of the flavin-binding GDH of the invention is 30-40° C., with the most preferred temperature being 37° C.
(e) Km Value for D-Glucose
Using the activity measuring method described above, the activity was measured with variable concentration of the substrate D-glucose, and the Michaelis constant (Km) was determined from a Lineweaver-Burk plot. As a result, the Km for D-glucose was 31.1 mM with MpGDH, 26.4 mM with MjGDH and 33.2 mM with McGDH.

(f) Thermostability

Figure 4:
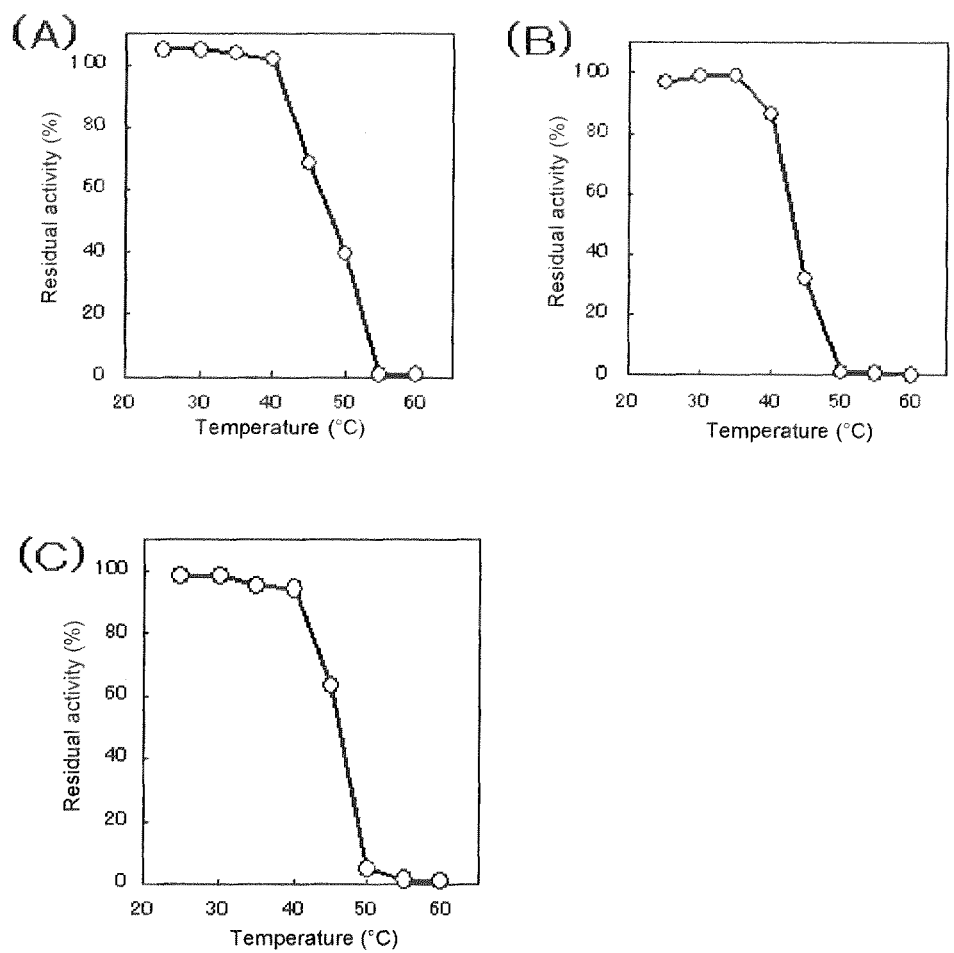
FIG. 4 is a graph showing the thermostability for a flavin-binding GDH of the invention.

The results for thermostability after treatment of the flavin-binding GDH enzymes of the invention for 15 minutes at each temperature, using 100 mM potassium acetate buffer (pH 5.0), are shown in FIG. 4 (FIG. 4(A) shows the results for MpGDH, (B) for MjGDH and (C) for McGDH). The flavin-binding GDH enzymes of the invention had residual activity of 80% or greater after heat treatment at 40° C. for 15 minutes, and were stable up to approximately 40° C.

(g) Stable pH Range

Figure 5:
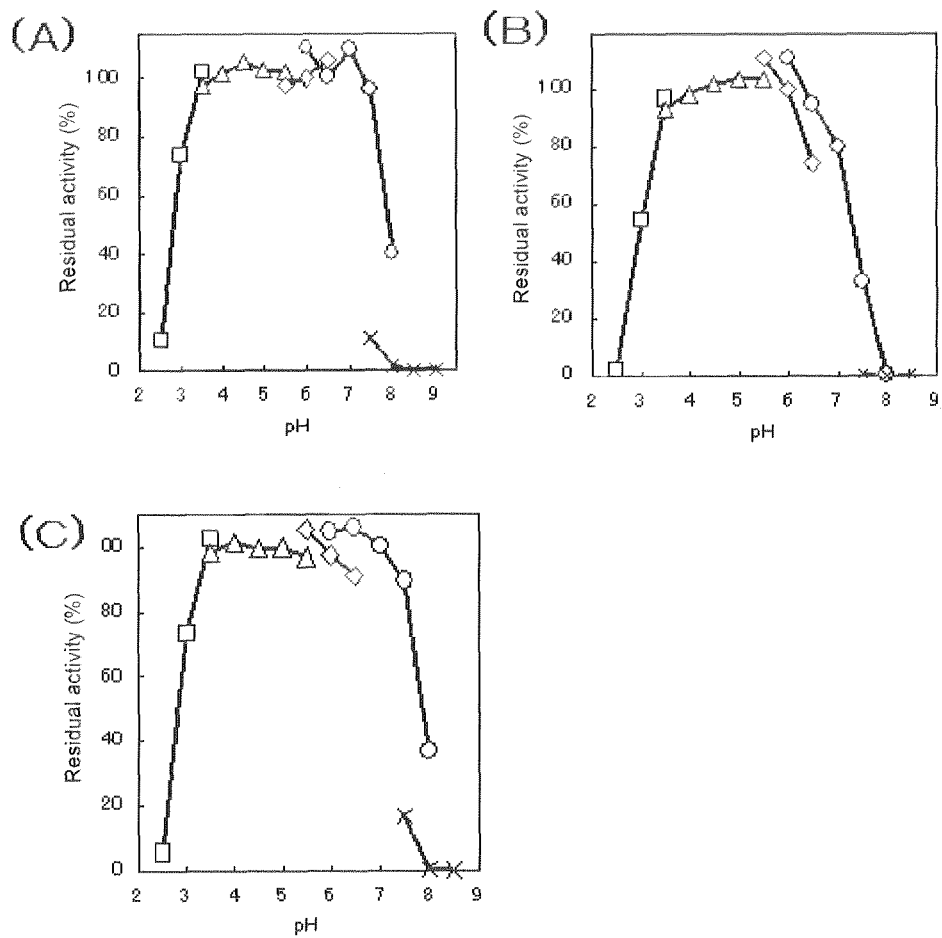
FIG. 5 is a graph showing the pH stability for a flavin-binding GDH of the invention.

The stable pH of the flavin-binding GDH of the invention was investigated. The results are shown in FIG. 5 (FIG. 5(A) is for MpGDH, (B) is for MjGDH and (C) is for McGDH). Specifically, 100 mM glycine-HCl buffer (pH 2.5-3.5, plotted as squares in the graphs), 100 mM potassium acetate buffer (pH 3.5-5.5, plotted as Δ in the graphs), 100 mM MES-NaOH buffer (pH 5.5-6.5, plotted as diamonds in the graphs), 100 mM potassium phosphate buffer (pH 6.0-8.0, plotted as circles in the graphs) and 100 mM Tris-HCl buffer (pH 7.5-9.0, plotted as x in the graphs) were used for measurement of residual activity of the flavin-binding GDH of the invention after treatment at 25° C. for 16 hours at different pHs. As a result, all of the enzymes had pH ranges of pH 3.5-7.0 for activity of at least 80% of the activity near pH 5.0, at which they exhibited maximum residual activity. The stable pH range for the flavin-binding GDH of the invention was therefore judged to be pH 3.5-7.0.

(h) Molecular Weight

Figure 6:
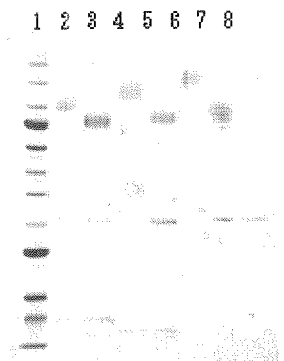
FIG. 6 shows the results of SDS-polyacrylamide electrophoresis of a flavin-binding GDH of the invention.

The molecular weights of MpGDH, MjGDH and McGDH were determined by SDS-polyacrylamide electrophoresis using 10-20% SuperSep Ace (product of Wako Pure Chemical Industries, Ltd.). Also, a deglycosylation kit (Enzymatic Deglycosylation Kit, product of PZM) was used for deglycosylation treatment of each flavin-binding GDH of the invention, and they were supplied for electrophoresis. The results are shown in FIG. 6. The electrophoresis samples were the following.

Lane 1: Molecular weight marker (product of New England Biolabs, Protein Ladder (10-250 kDa), 250 kDa, 150 kDa, 100 kDa, 80 kDa, 60 kDa, 50 kDa, 40 kDa, 30 kDa, kDa, 20 kDa, 15 kDa, from top).
Lane 2: MpGDH
Lane 3: Deglycosylated MpGDH
Lane 4: MjGDH
Lane 5: Deglycosylated MjGDH
Lane 6: McGDH
Lane 7: Deglycosylated McGDH
Lane 8: Enzyme used for deglycosylation reaction Based on FIG. 6, the molecular weights of the flavin-binding GDH enzymes of the invention were about 90-130 kDa for MpGDH, about 100-150 kDa for MjGDH and about 130-200 kDa for McGDH, and the molecular weights after removal of the sugar chains with the deglycosylation kit (Enzymatic Deglycosylation Kit, product of PZM) were all about 80 kDa for MpGDH, MjGDH and McGDH.

(i) Substrate Specificity

The activities of the flavin-binding GDH enzymes of the invention for different substrates were measured by the enzyme activity measuring method described in Example 1, using D-glucose, maltose, D-galactose, D-xylose, mannose, sucrose, trehalose, maltotriose and maltotetraose as substrates. The substrate concentrations were 50 mM. The results are shown in Table 3.

TABLE 3

Relative activities of GDH enzymes for different substrates

| | Relative activity (%) | | | | |
|---|---|---|---|---|---|
| Substrate | MpGDH | MjGDH | McGDH | Patent document 2 GDH | Patent document 3 GDH |
| D-Glucose | 100 | 100 | 100 | 100 | 100 |
| Maltose | 1.09 | 0.72 | 1.25 | 1.4 | 0.00 |
| D-Galactose | 0.44 | 0.54 | 1.25 | 1.2 | — |
| D-Xylose | 1.53 | 1.43 | 2.00 | 9.1 | 17.6 |
| Mannose | 0.66 | 0.36 | 1.00 | 2.8 | 1.40 |
| Sucrose | 0.00 | 0.36 | 0.25 | 0.1> | — |
| Trehalose | 0.22 | 0.00 | 0.25 | 1.7 | — |
| Maltotriose | 0.88 | 0.54 | 1.00 | — | — |
| Maltotetraose | 0.66 | 0.54 | 1.50 | — | — |

As a result, the flavin-invention GDH enzymes of the invention were judged to have very low reactivity for all of the different saccharide compounds, where the activity for D-glucose was defined as 100%. The activities for maltose, D-galactose and D-xylose were all 2% or lower.

(j) Inhibiting Effect by 1,10-Phenanthroline

The inhibiting effect of 10-phenanthroline on the activity of the flavin-binding GDH of the invention was examined in the following manner. The enzyme activity was determined by the enzyme activity measuring method of Example 1, but with addition of 1,10-phenanthroline to final concentrations of 1 mM, 5 mM, 10 mM 25 mM and 50 mM, and the inhibition rate was calculated against 0% as the inhibition rate without addition of 1,10-phenanthroline. The results are shown in Table 4.

TABLE 4

Inhibiting effect of 1,10-phenanthroline

| Final concentration of 1,10-phenanthroline (mM) | GDH inhibition rate (%) | | |
|---|---|---|---|
| | MpGDH | MjGDH | McGDH |
| 0 | 0 | 0 | 0 |
| 50 | 68.6 | 88.9 | 68.5 |
| 25 | 44.1 | 64.7 | 36.2 |
| 10 | 23.9 | 23.5 | 12.8 |
| 5 | 10.1 | 13.1 | 8.23 |
| 1 | 3.72 | 3.27 | 1.95 |

The inhibiting effect of 1,10-phenanthroline for the flavin-binding GDH of the invention was low, with only about a 2-4% inhibiting effect found with addition of 1 mM 1,10-phenanthroline and an inhibition rate of about 10% even at 5 mM concentration.

Example 4

Verifying Quantitation of Glucose Concentration Using Flavin-Binding GDH of the Invention, 1

Glucose measurement was conducted using flavin-binding GDH enzymes of the invention. Specifically, 1.79 mL of 100 mM phosphate buffer (pH 7.0), 0.08 mL of a D-glucose solution (250, 750, 1,250, 1,750, 2,500, 3,250, 4,000 or 5,000 mg/dL) and 0.01 mL of a 20 mM DCIP solution were mixed, the mixture was warmed at 37° C. for 5 minutes, and then 0.02 mL of a 20 mM PMS solution and 0.1 mL of 0.8 U/mL GDH solution were added and reaction was initiated. The relationship between glucose final concentration and reduction in absorbance at 600 nm (ΔA600) per minute as the enzyme reaction proceeded is shown in FIG. 7 (FIG. 7(A) shows the measurement results using MpGDH, (B) shows the measurement results using MjGDH, and (C) shows the measurement results using McGDH).

Figure 7:
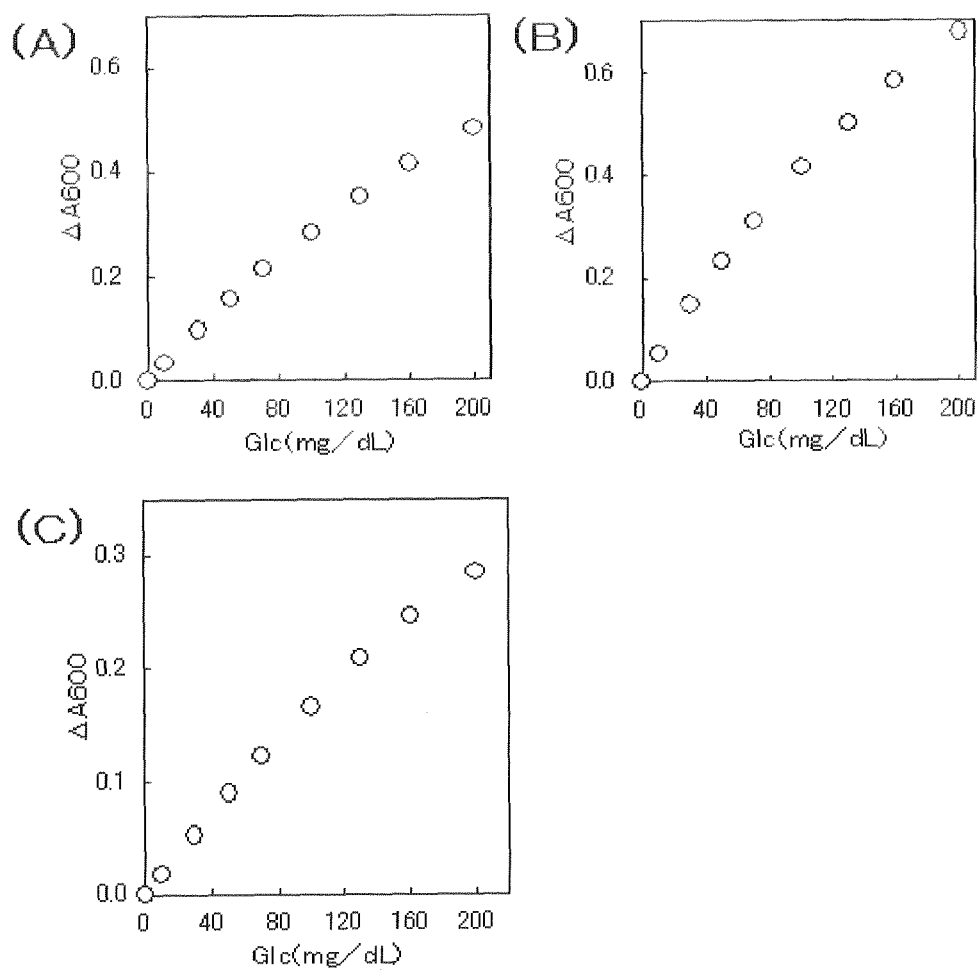
FIG. 7 is a graph showing the results of D-glucose level measurement, conducted using a flavin-binding GDH of the invention.

As seen in FIG. 7, it was confirmed that using a flavin-binding GDH enzyme of the invention allows highly precise measurement of glucose concentration in a measuring sample, for glucose final concentrations of up to 200 mg/dL.

Example 5

Verifying Quantitation of Glucose Concentration Using Flavin-Binding GDH of the Invention, 2

There were mixed 1.77 mL of 100 mM phosphate buffer (pH 7.0), 0.02 mL of a D-glucose solution (10,000 or 16,000 mg/dL) and 0.01 mL of a 20 mM DCIP solution. Next, 0.08 mL of maltose solution (3,000, 6,000, 9,000, 12,000 or 15,000 mg/dL), D-galactose solution (1,500, 3,000, 4,500, 6,000 or 7,500 mg/dL) or D-xylose solution (1,000, 2,000, 3,000, 4,000 or 5,000 mg/dL) was added and the mixture was warmed at 37° C. for 5 minutes, after which 0.02 mL of a 20 mM PMS solution and 0.1 mL of a 2.0 U/mL GDH solution were added, and reaction was initiated. Tables 5-7 show the relationship between reduction in absorbance at 600 nm ($\Delta A600$) per minute as the enzyme reaction proceeded, and final glucose concentration.

TABLE 5

Comparison of measured glucose values in samples containing different added saccharide compounds (Enzyme used: MpGDH)

| | | | | | | |
|---|---|---|---|---|---|---|
| D-Glucose concentration (mg/dL) | | | 100 | | | |
| Maltose concentration (mg/dL) | 0 | 120 | 240 | 360 | 480 | 600 |
| $\Delta A600$ | 0.394 | 0.393 | 0.398 | 0.398 | 0.399 | 0.401 |
| Relative value (%) | 100 | 100 | 101 | 101 | 101 | 102 |
| D-Glucose concentration (mg/dL) | | | 160 | | | |
| Maltose concentration (mg/dL) | 0 | 120 | 240 | 360 | 480 | 600 |
| $\Delta A600$ | 0.534 | 0.535 | 0.540 | 0.540 | 0.542 | 0.535 |
| Relative value (%) | 100 | 100 | 101 | 101 | 102 | 100 |
| D-Glucose concentration (mg/dL) | | | 100 | | | |
| D-Galactose concentration (mg/dL) | 0 | 60 | 120 | 180 | 240 | 300 |
| $\Delta A600$ | 0.394 | 0.392 | 0.393 | 0.393 | 0.393 | 0.394 |
| Relative value (%) | 100 | 100 | 100 | 100 | 100 | 100 |
| D-Glucose concentration (mg/dL) | | | 160 | | | |
| D-Galactose concentration (mg/dL) | 0 | 60 | 120 | 180 | 240 | 300 |
| $\Delta A600$ | 0.534 | 0.513 | 0.530 | 0.535 | 0.529 | 0.533 |
| Relative value (%) | 100 | 96 | 99 | 100 | 99 | 100 |
| D-Glucose concentration (mg/dL) | | | 100 | | | |
| D-Xylose concentration (mg/dL) | 0 | 40 | 80 | 120 | 160 | 200 |
| $\Delta A600$ | 0.394 | 0388 | 0.390 | 0.389 | 0.386 | 0.386 |
| Relative value (%) | 100 | 100 | 99 | 99 | 98 | 98 |
| D-Glucose concentration (mg/dL) | | | 160 | | | |
| D-Xylose concentration (mg/dL) | 0 | 40 | 80 | 120 | 160 | 200 |
| $\Delta A600$ | 0.534 | 0.530 | 0.529 | 0.525 | 0.527 | 0.522 |
| Relative value (%) | 100 | 99 | 99 | 98 | 99 | 98 |

TABLE 6

Comparison of measured glucose values in samples containing different added saccharide compounds (Enzyme used: MjGDH)

| | | | | | | |
|---|---|---|---|---|---|---|
| D-Glucose concentration (mg/dL) | | | 100 | | | |
| Maltose concentration (mg/dL) | 0 | 120 | 240 | 360 | 480 | 600 |
| $\Delta A600$ | 0.857 | 0.861 | 0.867 | 0.864 | 0.871 | 0.868 |
| Relative value (%) | 100 | 101 | 101 | 101 | 102 | 101 |
| D-Glucose concentration (mg/dL) | | | 160 | | | |
| Maltose concentration (mg/dL) | 0 | 120 | 240 | 360 | 480 | 600 |
| $\Delta A600$ | 1.222 | 1.230 | 1.222 | 1.234 | 1.228 | 1.238 |
| Relative value (%) | 100 | 101 | 100 | 101 | 101 | 101 |
| D-Glucose concentration (mg/dL) | | | 100 | | | |
| D-Galactose concentration (mg/dL) | 0 | 60 | 120 | 180 | 240 | 300 |
| $\Delta A600$ | 0.857 | 0.863 | 0.864 | 0.865 | 0.863 | 0.854 |

TABLE 6-continued

Comparison of measured glucose values in samples containing different added saccharide compounds (Enzyme used: MjGDH)

| | | | | | | |
|---|---|---|---|---|---|---|
| Relative value (%) | 100 | 161 | 101 | 101 | 101 | 100 |
| D-Glucose concentration (mg/dL) | | | 160 | | | |
| D-Galactose concentration (mg/dL) | 0 | 60 | 120 | 180 | 240 | 300 |
| ΔA600 | 1.222 | 1.226 | 1.222 | 1.224 | 1.216 | 1.214 |
| Relative value (%) | 100 | 100 | 100 | 100 | 100 | 99 |
| D-Glucose concentration (mg/dL) | | | 100 | | | |
| D-Xylose concentration (mg/dL) | 0 | 40 | 80 | 120 | 160 | 200 |
| ΔA600 | 0.857 | 0.869 | 0.851 | 0.847 | 0.857 | 0.856 |
| Relative value (%) | 100 | 101 | 99 | 100 | 100 | 100 |
| D-Glucose concentration (mg/dL) | | | 160 | | | |
| D-Xylose concentration (mg/dL) | 0 | 40 | 80 | 120 | 160 | 200 |
| ΔA600 | 1.222 | 1.234 | 1.212 | 1.222 | 1.212 | 1.218 |
| Relative value (%) | 100 | 101 | 99 | 100 | 99 | 100 |

TABLE 7

Comparison of measured glucose values in samples containing different added saccharide compounds (Enzyme used: MjGDH)

| | | | | | | |
|---|---|---|---|---|---|---|
| D-Glucose concentration (mg/dL) | | | 100 | | | |
| Maltose concentration (mg/dL) | 0 | 120 | 240 | 360 | 480 | 600 |
| ΔA600 | 0.431 | 0.434 | 0.443 | 0.444 | 0.443 | 0.444 |
| Relative value (%) | 100 | 101 | 103 | 103 | 103 | 103 |
| D-Glucose concentration (mg/dL) | | | 160 | | | |
| Maltose concentration (mg/dL) | 0 | 120 | 240 | 360 | 480 | 600 |
| ΔA600 | 0.637 | 0.646 | 0.649 | 0.654 | 0.652 | 0.653 |
| Relative value (%) | 100 | 101 | 102 | 103 | 102 | 103 |
| D-Glucose concentration (mg/dL) | | | 100 | | | |
| D-Galactose concentration (mg/dL) | 0 | 60 | 120 | 180 | 240 | 300 |
| ΔA600 | 0.431 | 0.437 | 0.438 | 0.439 | 0.443 | 0.441 |
| Relative value (%) | 100 | 101 | 102 | 102 | 103 | 102 |
| D-Glucose concentration (mg/dL) | | | 160 | | | |
| D-Galactose concentration (mg/dL) | 0 | 60 | 120 | 180 | 240 | 300 |
| ΔA600 | 0.637 | 0.644 | 0.646 | 0.639 | 0.645 | 0.640 |
| Relative value (%) | 100 | 101 | 101 | 100 | 101 | 101 |
| D-Glucose concentration (mg/dL) | | | 100 | | | |
| D-Xylose concentration (mg/dL) | 0 | 40 | 80 | 120 | 160 | 200 |
| ΔA600 | 0.431 | 0.439 | 0.440 | 0.443 | 0.442 | 0.435 |
| Relative value (%) | 100 | 102 | 102 | 103 | 103 | 101 |
| D-Glucose concentration (mg/dL) | | | 160 | | | |
| D-Xylose concentration (mg/dL) | 0 | 40 | 80 | 120 | 160 | 200 |
| ΔA600 | 0.637 | 0.644 | 0.645 | 0.643 | 0.646 | 0.642 |
| Relative value (%) | 100 | 101 | 101 | 101 | 101 | 101 |

Tables 5-7 show that the GDH enzymes of the invention allow highly accurate quantitation of glucose concentrations in samples containing maltose up to a final concentration of 600 mg/dL, D-galactose up to a final concentration of 300 mg/dL or D-xylose up to a final concentration of 200 mg/dL.

Example 6

Verifying Quantitation of Glucose Concentration Using Flavin-Binding GDH of the Invention, 3

There were mixed 1.61 mL of 100 mM phosphate buffer (pH 7.0), 0.02 mL of a D-glucose solution (10,000 or 16,000 mg/dL) and 0.01 mL of a 20 mM DCIP solution. Next, 0.08 mL each of maltose solution (3,000, 6,000, 9,000, 12,000 or 15,000 mg/dL), D-galactose solution (1,500, 3,000, 4,500, 6,000 or 7,500 mg/dL) and D-xylose solution (1,000, 2,000, 3,000, 4,000 or 5,000 mg/dL) was added and the mixture was warmed at 37° C. for 5 minutes, after which 0.02 mL of a 20 mM PMS solution and 0.1 mL of a 2.0 U/mL solution of flavin-binding GDH of the invention were added, and reaction was initiated. Tables 8 and 9 show the relationship between reduction in absorbance at 600 nm ($\Delta A600$) per minute as the enzyme reaction proceeded, and final glucose concentration.

TABLE 8

Comparison of measured glucose values in samples containing 3 different added saccharide compounds (Enzyme used: MpGDH)

| | | | | | | |
|---|---|---|---|---|---|---|
| D-Glucose concentration (mg/dL) | | | 100 | | | |
| Maltose concentration (mg/dL) | 0 | 120 | 240 | 360 | 480 | 600 |
| D-Galactose concentration (mg/dL) | 0 | 60 | 120 | 180 | 240 | 300 |
| D-Xylose concentration (mg/dL) | 0 | 40 | 80 | 120 | 160 | 200 |
| $\Delta A600$ | 0.637 | 0.640 | 0.644 | 0.650 | 0.652 | 0.647 |
| Relative value (%) | 100 | 101 | 101 | 102 | 102 | 102 |
| D-Glucose concentration (mg/dL) | | | 160 | | | |
| Maltose concentration (mg/dL) | 0 | 120 | 240 | 360 | 480 | 600 |
| D-Galactose concentration (mg/dL) | 0 | 60 | 120 | 180 | 240 | 300 |
| D-Xylose concentration (mg/dL) | 0 | 40 | 80 | 120 | 160 | 200 |
| $\Delta A600$ | 0.726 | 0.747 | 0.750 | 0.750 | 0.748 | 0.755 |
| Relative value (%) | 100 | 103 | 103 | 103 | 103 | 104 |

TABLE 9

Comparison of measured glucose values in samples containing 3 different added saccharide compounds (Enzyme used: MjGDH)

| | | | | | | |
|---|---|---|---|---|---|---|
| D-Glucose concentration (mg/dL) | | | 100 | | | |
| Maltose concentration (mg/dL) | 0 | 120 | 240 | 360 | 480 | 600 |
| D-Galactose concentration (mg/dL) | 0 | 60 | 120 | 180 | 240 | 300 |
| D-Xylose concentration (mg/dL) | 0 | 40 | 80 | 120 | 160 | 200 |
| $\Delta A600$ | 0.746 | 0.722 | 0.728 | 0.734 | 0.725 | 0.734 |
| Relative value (%) | 100 | 97 | 98 | 98 | 97 | 98 |
| D-Glucose concentration (mg/dL) | | | 160 | | | |
| Maltose concentration (mg/dL) | 0 | 120 | 240 | 360 | 480 | 600 |
| D-Galactose concentration (mg/dL) | 0 | 60 | 120 | 180 | 240 | 300 |
| D-Xylose concentration (mg/dL) | 0 | 40 | 80 | 120 | 160 | 200 |
| $\Delta A600$ | 1.076 | 1.049 | 1.052 | 1.058 | 1.067 | 1.070 |
| Relative value (%) | 100 | 97 | 98 | 98 | 99 | 99 |

Tables 8 and 9 show that MpGDH and MjGDH allow very highly accurate quantitation of glucose concentrations in samples containing maltose up to a final concentration of 600 mg/dL, D-galactose up to a final concentration of 300 mg/dL or D-xylose up to a final concentration of 200 mg/dL.

Example 7

Cloning of *Mucor*-Derived Flavin-Binding GDH Gene and Expression in Transformants (1) Preparation of mRNA

*Mucor* prainii NISL0103 was seeded in 3 mL of malt extract culture medium (2.0% malt extract, 4.0% glucose, 0.1% polypeptone, pH 6.0), and shake cultured for 2 days at 30° C. The culture solution was filtered with filter paper and the mycelium was recovered. The obtained hyphae were frozen in liquid nitrogen and a mortar was used to crush them. Next, ISOGEN (product of Nippon Gene Co., Ltd.) was used to obtain mRNA from the crushed cells according to the protocol described in the kit.

(2) Determination of Amino Acid Sequence of GDH Portion

The MpGDH obtained from Example 2 was supplied to SuperSep Ace 10-20% (product of Wako Pure Chemical Industries, Ltd.) for electrophoresis. The electrophoresed gel was stained using Quick-CBB (product of Wako Pure Chemical Industries, Ltd.), and the band corresponding to the molecular weight of the enzyme was cut out. The cut-out gel section was consigned to an outside agency, and the amino acid sequence information for the protein contained therein was obtained. The obtained amino acid sequences were LVENFTPPTPAQIE (SEQ ID NO: 5) and IRNSTDEWANYY (SEQ ID NO: 6).

(3) Determination of GDH Gene Sequence

Based on the partial amino acid sequence information, degenerate primers comprising mixed bases (examples of the primers are listed as SEQ ID NO: 7 (forward primer) and SEQ ID NO: 8 (reverse primer)) were constructed. The mixed bases represented as single letters in SEQ ID NO: 7 and 8 are h=a+c+t, r=a+g, y=c+t and d=a+g+t. Using mRNA from the *Mucor prainii* NISL0103 prepared in (1) above as template, RT-PCR was conducted with a PrimeScript RT-PCR Kit (product of Takara Bio, Inc.), according to the protocol described in the kit. The oligo-dT primer included in the kit was used for the reverse transcription reaction, and the degenerate primers listed as SEQ ID NO: 7 and 8 were used for cDNA amplification by PCR. When the reaction mixture was supplied for agarose gel electrophoresis, a single band was confirmed corresponding to a length of about 800 bp. The amplified DNA fragment in the band was purified, and a Ligation Convenient Kit (product of Nippon Gene Co., Ltd.) was used for ligation of the amplified DNA fragment to pT7Blue (Novagen), to construct recombinant plasmid pTMGD-1.

The obtained pTMGD-1 was then used to transform competent cells of *E. coli* JM109 (product of Nippon Gene Co., Ltd.) by a known heat shock method. A GenElute Plasmid Miniprep Kit (product of Sigma) was used for extraction and purification of the plasmids from the obtained transformants, and the nucleotide sequence of the amplified DNA fragment in the plasmids was determined (767 bp).

Based on the sequence data for the obtained amplified DNA fragment, an unknown region of the GDH gene at the 3'-end was determined using a 3'-Full RACE Core Set (product of Takara Bio, Inc.), and an unknown region of the GDH gene at the 5'-end was determined using a 5'-Full RACE Core Set (product of Takara Bio, Inc.). Both of these were determined following the protocol described in the kit, using the 3-site adaptor-primer supplied with the kit and the primer listed as SEQ ID NO: 9, for the 3'-Full RACE Core Set, and the primers listed as SEQ ID NO: 10, 11, 12, 13 and 14 for the 5'-Full RACE Core Set. As a result of nucleotide sequence analysis of the DNA fragments in multiple plasmids obtained by this method, the full-length 1926 bp *Mucor prainii* NISL0103-derived GDH gene sequences listed as SEQ ID NO: 2 and SEQ ID NO: 4 were elucidated. The amino acid sequences of the enzyme gene as predicted from the gene sequences are listed as SEQ ID NO: 1 and SEQ ID NO: 3.

(4) Transformation of *E. coli* and Confirmation of GDH Activity

An N-terminal region primer (SEQ ID NO: 15) and C-terminal region primer (SEQ ID NO: 16) were constructed, and the primers were used with the *Mucor prainii* NISL0103 mRNA prepared in (1) above for RT-PCR.

When the reaction mixture was supplied for agarose gel electrophoresis, a single band was confirmed corresponding to a length of about 2 kbp. The amplified DNA fragment in the band was purified and ligated with plasmid pUC19 (product of Takara Bio, Inc.) that had been digested with restriction enzyme SmaI, to construct recombinant plasmid puc-MGD.

The obtained recombinant plasmid puc-MGD was used to transform competent cells of *E. coli* JM109 (product of Nippon Gene Co., Ltd.) by a known heat shock method. The transformed *E. coli* JM109 (puc-MGD) cells were then shake cultured at 37° C. for 2 hours in 10 mL of TY culture medium (1% bactotryptone, 0.5% Bacto Yeast Extract, 0.5% NaCl, pH 7.0) containing 100 μg/mL ampicillin, and IPTG was added to a final concentration of 1 mM, prior to further shake culturing at 30° C. for 6 hours.

The culture solution was disrupted by 4 periods of treatment for 20 seconds each using an ultrasonic disruptor (Ultrasonic Generator, product of Nissei) while cooling on ice. The disrupted solution was placed in an Eppendorf tube, and a microcentrifuge was used for centrifugal separation at 12,000 rpm for 10 minutes, after which the supernatant fraction was transferred to a separate Eppendorf tube as a crude enzyme solution. Measurement of the GDH activity in the crude enzyme solution by this enzyme activity measuring method confirmed the flavin-binding GDH activity of the invention.

(5) Transformation of *Aspergillus* and Confirmation of GDH Activity

Double-joint PCR (Fungal Genetics and Biology, 2004, Vol. 41, p 973-981) was conducted to construct a cassette comprising 5' arm region-PyrG gene (uracil auxotrophic marker)-TEF1 promoter gene-flavin-binding GDH gene-3' arm region, and *Aspergillus sojae* KK1-2 was used as the host for transformation by the protoplast-PEG method. The target transformants were confirmed and screened from among the obtained cell lines by PCR.

After taking 5 g of 0.8%-water sprinkled wheat bran in a 150 mL Erlenmeyer flask, it was closed with a cotton plug and subjected to autoclave sterilization at 121° C. for 50 minutes. Into this there were inoculated the transformants in which the flavin-binding GDH gene of the invention had been transferred, or a conidial suspension of a control strain, to $1 \times 10^5$/g malt, and culturing was carried out at 30° C. for 64 hours. A non-transformed host was used as the control strain.

After adding a 5-fold amount of 10 mM acetate buffer (pH 5.0) to 2 g of the bran malt after culturing, the mixture was mashed at 30 seconds×8 times using a Polytron homogenizer PT3000 (product of Kinematica AG). The mashing was followed by centrifugal separation at 14,000 rpm for 30 minutes, and the obtained supernatant fraction was used as a crude enzyme solution. Upon measuring the GDH activity in the crude enzyme solution by the enzyme activity-measuring method described above, the GDH activity of the crude enzyme solution obtained using the control strain was found to be 0.3 U/mL, while the GDH activity of the crude enzyme solution obtained using the transformants was 14.0 U/mL, thus confirming that the flavin-binding GDH of the invention is expressed in transformants.

The transformants in which the flavin-binding GDH genes of the invention had been inserted were used for measurement of GDH activity for different substrates. Measurement was performed by the enzyme activity measuring method described in Example 1, using D-glucose, maltose, D-galactose, D-xylose, mannose, sucrose and trehalose as substrates. The substrate concentrations were 50 mM. The results are shown in Table 10.

TABLE 10

Relative activity of GDH of invention for different substrates

| Substrate | Relative activity (%) |
|---|---|
| D-Glucose | 100 |
| Maltose | 1.02 |
| D-Galactose | 0.71 |
| D-Xylose | 1.73 |

TABLE 10-continued

Relative activity of GDH of invention for different substrates

| Substrate | Relative activity (%) |
|---|---|
| Mannose | 0.63 |
| Sucrose | 0.16 |
| Trehalose | 0.16 |

As a result, the flavin-binding GDH enzymes of the invention were judged to have very low reactivity for all of the various saccharide compounds, where the activity for D-glucose was defined as 100%. The activities for maltose, D-galactose and D-xylose were all 2% or lower.

INDUSTRIAL APPLICABILITY

The flavin-binding GDH enzymes of the invention have very high substrate specificity for D-glucose and sufficiently low reactivity for saccharide compounds other than D-glucose (maltose, D-galactose, D-xylose), and therefore allow highly accurate quantitation of D-glucose concentrations even when measuring samples containing saccharide compounds other than D-glucose, and are useful in fields such as measurement of blood glucose levels and quantitation of glucose concentrations in foods.

The invention claimed is:

1. A flavin-binding glucose dehydrogenase having the following properties (i) to (iii):
   (i) action: glucose dehydrogenase activity is exhibited in the presence of an electron acceptor,
   (ii) molecular weight: the molecular weight of the polypeptide chain portion of the protein is approximately 80 kDa,
   (iii) substrate specificity: the flavin-binding glucose dehydrogenase has a low reactivity for maltose, D-galactose and D-xylose, with respect to its reactivity for D-glucose,
   wherein the flavin-binding glucose dehydrogenase has an optimum pH of 6.5 to 7.0, an optimum temperature of 37 to 40° C., a stable pH range of 3.5 to 7.0 and a residual activity of at least 80% after heat treatment at 40° C. for 15 minutes.

2. A flavin-binding glucose dehydrogenase according to claim 1, wherein the reactivity for any of maltose, D-galactose and D-xylose is no greater than 2%, where the reactivity for D-glucose is defined as 100%.

3. A flavin-binding glucose dehydrogenase according to claim 1 or 2, wherein the reactivity for D-glucose, when one or more of the following saccharide compounds (a) to (c) are present:
   (a) maltose
   (b) D-galactose
   (c) D-xylose
   is 96%-104%, where the reactivity for D-glucose in the absence of (a) to (c) is defined as 100%.

4. A flavin-binding glucose dehydrogenase according to claim 3, which is derived from a microorganism in a classification selected from the group consisting of subphylum Mucormycotina, class Mucormycetes, order Mucorales, and family Mucoraceae.

5. A flavin-binding glucose dehydrogenase according to claim 4, which is derived from a microorganism classified as genus *Mucor*.

6. A flavin-binding glucose dehydrogenase according to claim 1 or 2, which is derived from a microorganism in a classification selected from the group consisting of subphylum Mucormycotina, class Mucoromycetes, order Mucorales and family Mucoraceae.

7. A flavin-binding glucose dehydrogenase according to claim 6, which is derived from a microorganism classified as genus *Mucor*.

8. A flavin-binding glucose dehydrogenase, which has (i) an amino acid sequence selected from the group consisting of SEQ ID NO: 1 and SEQ ID NO: 3, or (ii) an amino acid sequence having at least 90% identity with the amino acid sequence (i).

9. A flavin-binding glucose dehydrogenase gene comprising a DNA selected from the group consisting of
   (A) a DNA coding for the amino acid sequence SEQ ID NO: 1;
   (B) a DNA comprising the nucleotide sequence SEQ ID NO: 2;
   (C) a DNA coding for the amino acid sequence SEQ ID NO: 3;
   (D) a DNA comprising the nucleotide sequence SEQ ID NO: 4;
   (E) a DNA having a nucleotide sequence with at least 90% identity with the nucleotide sequence SEQ ID NO: 2 or SEQ ID NO: 4 and coding for a protein having flavin-binding glucose dehydrogenase enzyme activity.

10. A recombinant DNA comprising a flavin-binding glucose dehydrogenase gene according to claim 9 inserted into vector DNA.

11. A transformant having the recombinant DNA according to claim 10 introduced therein.

12. A method for producing a flavin-binding glucose dehydrogenase having low reactivity for maltose, D-galactose and D-xylose with respect to its reactivity for D-glucose, wherein a microorganism comprising a flavin-binding glucose dehydrogenase gene according to claim 10 or recombinant DNA according to claim 10 and capable of producing flavin-binding glucose dehydrogenase is cultured, and the flavin-binding glucose dehydrogenase is obtained from the culture.

13. A method for producing a flavin-binding glucose dehydrogenase according to claim 1 or 2, wherein a microorganism classified as genus *Mucor* is cultured in a culture medium, and the flavin-binding glucose dehydrogenase is obtained from the microbial cells.

14. A method for producing a flavin-binding glucose dehydrogenase according to claim 13, wherein the microorganism is one or more microorganisms selected from the group consisting of *Mucor prainii, Mucor javanicus* and *Mucor circinelloides f. circinelloides*.

15. A method for producing a flavin-binding glucose dehydrogenase according to claim 3, wherein a microorganism classified as genus *Mucor* is cultured in a culture medium, and the flavin-binding glucose dehydrogenase is obtained from the microbial cells.

16. A method for producing a flavin-binding glucose dehydrogenase according to claim 15, wherein the microorganism is one or more microorganisms selected from the group consisting of *Mucor prainii, Mucor javanicus* and *Mucor circinelloides f. circinelloides*.

17. A method for producing a flavin-binding glucose dehydrogenase according to claim 6, wherein a microorganism classified as genus *Mucor* is cultured in a culture medium, and the flavin-binding glucose dehydrogenase is obtained from the microbial cells.

18. A method for producing a flavin-binding glucose dehydrogenase according to claim 17, wherein the microorganism is one or more microorganisms selected from the group consisting of *Mucor prainii, Mucor javanicus* and *Mucor circinelloides f. circinelloides*.

19. A method for producing a flavin-binding glucose dehydrogenase according to claim 6, wherein a microorganism classified as genus *Mucor* is cultured in a culture medium, and the flavin-binding glucose dehydrogenase is obtained from the microbial cells.

20. A method for producing a flavin-binding glucose dehydrogenase according to claim 19, wherein the microorganism is one or more microorganisms selected from the group consisting of *Mucor prainii, Mucor javanicus* and *Mucor circinelloides f. circinelloides*.

* * * * *

SEQUENCE LISTING

```
<160> NUMBER OF SEQ ID NOS: 16

<210> SEQ ID NO 1
<211> LENGTH: 641
<212> TYPE: PRT
<213> ORGANISM: Mucor prainii

<400> SEQUENCE: 1

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Ser Thr Asp Thr Tyr
            20                  25                  30

Asp Tyr Val Thr Val Gly Gly Gly Val Ala Gly Leu Ala Leu Ala Ser
        35                  40                  45

Arg Ile Ser Glu Asn Lys Asp Val Thr Val Ala Val Leu Glu Ser Gly
    50                  55                  60

Pro Asn Ala Asn Asp Arg Phe Val Val Tyr Ala Pro Gly Met Tyr Gly
65                  70                  75                  80

Gln Ala Val Gly Thr Asp Leu Cys Pro Leu Ile Pro Thr Thr Pro Gln
                85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
        115                 120                 125

Lys Asp Tyr Asp Ala Trp Glu Glu Leu Gly Asn Pro Gly Trp Asn Gly
    130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
            180                 185                 190
```

-continued

```
Gln Ser Ala Ser Trp Asn Ala Ser Leu Glu Thr Leu Asp Phe Thr Ala
        195                 200                 205
Leu Pro Asp Ile Leu Asn Gly Thr Leu Ala Gly Tyr Ser Thr Thr Pro
    210                 215                 220
Asn Ile Leu Asp Pro Glu Thr Val Gln Arg Val Asp Ser Tyr Thr Gly
225                 230                 235                 240
Tyr Ile Ala Pro Tyr Thr Ser Arg Asn Leu Asn Val Leu Ala Asn
                245                 250                 255
His Thr Val Ser Arg Ile Gln Phe Ala Pro Lys Asn Gly Ser Glu Pro
            260                 265                 270
Leu Lys Ala Thr Gly Val Glu Trp Pro Thr Gly Asn Lys Asn Gln
        275                 280                 285
Lys Gln Ile Ile Lys Ala Arg Tyr Glu Val Ile Ser Ser Gly Ala
    290                 295                 300
Ile Gly Ser Pro Lys Leu Leu Glu Ile Ser Gly Ile Gly Asn Lys Asp
305                 310                 315                 320
Ile Val Ser Ala Ala Gly Val Glu Ser Leu Ile Asp Leu Pro Gly Val
                325                 330                 335
Gly Ser Asn Met Gln Asp His Val His Ala Ile Thr Val Ser Thr Thr
            340                 345                 350
Asn Ile Thr Gly Tyr Thr Thr Asn Ser Val Phe Val Asn Glu Thr Leu
        355                 360                 365
Ala Gln Glu Gln Arg Glu Gly Tyr Glu Ala Asn Lys Thr Gly Ile Trp
    370                 375                 380
Ala Thr Thr Pro Asn Asn Leu Gly Tyr Pro Thr Pro Glu Gln Leu Phe
385                 390                 395                 400
Asn Gly Thr Glu Phe Val Ser Gly Lys Glu Phe Ala Asp Lys Ile Arg
                405                 410                 415
Asn Ser Thr Asp Glu Trp Ala Asn Tyr Tyr Ala Ser Thr Asn Ala Ser
            420                 425                 430
Asn Val Glu Leu Leu Lys Lys Gln Tyr Ala Ile Val Ala Ser Arg Tyr
        435                 440                 445
Glu Glu Asn Tyr Leu Ser Pro Ile Glu Ile Asn Phe Thr Pro Gly Tyr
    450                 455                 460
Glu Gly Ser Gly Asn Val Asp Leu Gln Asn Asn Lys Tyr Gln Thr Val
465                 470                 475                 480
Asn His Val Leu Ile Ala Pro Leu Ser Arg Gly Tyr Thr His Ile Asn
                485                 490                 495
Ser Ser Asp Val Glu Asp His Ser Val Ile Asn Pro Gln Tyr Tyr Ser
            500                 505                 510
His Pro Met Asp Ile Asp Val His Ile Ala Ser Thr Lys Leu Ala Arg
        515                 520                 525
Glu Ile Ile Thr Ala Ser Pro Gly Leu Gly Asp Ile Asn Ser Gly Glu
    530                 535                 540
Ile Glu Pro Gly Met Asn Ile Thr Ser Glu Asp Leu Arg Ser Trp
545                 550                 555                 560
Leu Ser Asn Asn Val Arg Ser Asp Trp His Pro Val Gly Thr Cys Ala
                565                 570                 575
Met Leu Pro Lys Glu Leu Gly Gly Val Val Ser Pro Ala Leu Met Val
            580                 585                 590
Tyr Gly Thr Ser Asn Leu Arg Val Val Asp Ala Ser Ile Met Pro Leu
        595                 600                 605
Glu Val Ser Ser His Leu Met Gln Pro Thr Tyr Gly Ile Ala Glu Lys
```

```
                610              615              620
Ala Ala Asp Ile Ile Lys Asn Phe Tyr Lys Thr Gln His Lys Asn Gln
625              630              635              640

Asn

<210> SEQ ID NO 2
<211> LENGTH: 1926
<212> TYPE: DNA
<213> ORGANISM: Mucor prainii

<400> SEQUENCE: 2
atgaagatca cagctgccat tatcactgtt gccacagcat ttgcttcttt tgcttctgct      60
caacaagaca caaattcttc ctcaactgat acttatgatt atgttaccgt tggcggcggt     120
gtagctggtt tggctttggc tagtcgtatc tctgaaaaca aggatgtcac tgttgctgtt     180
ctcgagtccg gtcctaatgc caatgataga tttgttgttt atgctcctgg catgtatggc     240
caagctgttg gcactgatct ctgtcctctc attcctacta ctcctcaaga aaatatgggc     300
aacagaagtc tcacaatcgc tactggtaga ttgctcggtg gtggcagtgc tattaatggt     360
cccgttagga cccgtggtgg cttgaaggat tacgatgctt gggaggagct cggtaaccct     420
ggatggaacg gtgccaactt gttcaagtac tttaagaagg tcgaaaactt cactcctcct     480
actcctgcac aaattgaata cggcgctact tatcagaaaa gtgctcatgg caagaaggga     540
cvtattgatg tctctttcac gaactacgag ttctctcaat ctgctagctg aacgcctca     600 ctcgaaaccc ttgatttcac tgcacttcct gatatcttga acggtacttt ggccggttac     660
tctaccactc ccaacatttt ggaccctgag actgttcaac gtgttgattv ctatactggt     720
tacattgctc cttacactag ccgtaacaac ctcaatgttt tggccaacca taccgtctcc     780
cgcattcaat ttgctcccaa gaatggtagc gaacctctca aggctaccgg tgttgaatgg     840
tatcccactg gcaacaagaa tcaaaagcaa attatcaagg cccgttatga agttatcatc     900
tcatctggtg ccattggtag tcctaagctt ttggaaatct ctggtatcgg taataaggat     960
atcgtctctg ctgctggcgt cgagtccttg attgacttgc ctggcgttgg ttccaacatg    1020
caagatcacg ttcatgctat cactgtctct actaccaata ttactggcta tactaccaac    1080
agcgtctttg tcaatgaaac ccttgcccaa gaacaaagag aagaatatga agccaacaag    1140
actggtatct gggctactac tcccaacaac ctcggttatc ctacgcccga caactcttc    1200 aatggcaccg aattcgtttc tggaaaggag tttgctgaca agattcgtaa ctctactgat    1260
gaatgggcca actattatgc tactaccaac gcctccaatg tcgagttatt aaagaagcaa    1320
tatgctattg tcgcctctcg ttacgaagag aactacttgt ctcctattga aatcaacttc    1380
actcctggtt atgagggtag cggtaatgtc gatttgcaaa acaacaagta ccaaactgtc    1440
aaccatgtct tgattgctcc tttaagtcgt ggttatactc acattaactc ttctgatgtg    1500
gaggatcatt ctgtcattaa tccccaatac tactctcatc ctatggatat tgatgtccat    1560
atcgcttcca ctaaacttgc tcgcgaaatc atcactgcct ctcccggtct tggtgacatt    1620
aacagtggcg aaaacgaacc cggtatgaat attacttctg aagacgacct tagatcttgg    1680
ttgagtaata atgtccgttc tgactggcat cctgttggta cttgtgctat gcttcccaag    1740
gaattaggtg gtgttgtcag ccccgctctc atggtttacg gcacttccaa cttgcgtgtt    1800
gttgatgctt cgattatgcc cctcgaagtc tcttctcatt tgatgcaacc cacctacggt    1860
attgctgaga aggctgctga cattattaag aatttctaca agactcaaca caagaaccaa    1920
aattag                                                                1926
```

<210> SEQ ID NO 3
<211> LENGTH: 641
<212> TYPE: PRT
<213> ORGANISM: Mucor prainii

<400> SEQUENCE: 3

```
Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Thr Asp Thr Tyr
            20                  25                  30

Asp Tyr Val Ile Val Gly Gly Gly Val Ala Gly Leu Ala Leu Ala Ser
                35                  40                  45

Arg Ile Ser Glu Asn Lys Asp Val Thr Val Ala Val Leu Glu Ser Gly
    50                  55                  60

Pro Asn Ala Asn Asp Arg Phe Val Val Tyr Ala Pro Gly Met Tyr Gly
65                  70                  75                  80

Gln Ala Val Gly Thr Asp Leu Cys Pro Leu Ile Pro Thr Thr Pro Gln
                85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
        115                 120                 125

Lys Asp Tyr Asp Ala Trp Glu Glu Leu Gly Asn Pro Gly Trp Asn Gly
    130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
            180                 185                 190

Gln Ser Ala Ser Trp Asn Ala Ser Leu Glu Thr Leu Asp Phe Thr Ala
        195                 200                 205

Leu Pro Asp Ile Leu Asn Gly Thr Leu Ala Gly Tyr Ser Thr Thr Pro
    210                 215                 220

Asn Ile Leu Asp Pro Glu Thr Val Gln Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
            260                 265                 270

Leu Lys Ala Thr Gly Val Glu Trp Tyr Pro Thr Gly Asn Lys Asn Gln
        275                 280                 285

Lys Gln Ile Ile Lys Ala Arg Tyr Glu Val Ile Ile Ser Ser Gly Ala
    290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
            340                 345                 350

Asn Ile Thr Gly Tyr Thr Thr Asn Ser Val Phe Val Asn Glu Thr Leu
        355                 360                 365

Ala Gln Glu Gln Arg Glu Glu Tyr Glu Ala Asn Lys Thr Gly Ile Trp
    370                 375                 380
```

Ala Thr Thr Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
            405                 410                 415

Asn Ser Thr Asp Glu Trp Ala Asn Tyr Tyr Ala Ser Thr Asn Ala Ser
        420                 425                 430

Asn Val Glu Leu Leu Lys Lys Gln Tyr Ala Ile Val Ala Ser Arg Tyr
    435                 440                 445

Glu Glu Asn Tyr Leu Ser Pro Ile Glu Ile Asn Phe Thr Pro Gly Tyr
        450                 455                 460

Glu Gly Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
            485                 490                 495

Ser Ser Asp Val Glu Asp His Ser Val Ile Asn Pro Gln Tyr Tyr Ser
        500                 505                 510

His Pro Met Asp Ile Asp Val His Ile Ala Ser Thr Lys Leu Ala Arg
    515                 520                 525

Glu Ile Ile Thr Ala Ser Pro Gly Leu Gly Asp Ile Asn Ser Gly Glu
        530                 535                 540

Ile Glu Pro Gly Met Asn Ile Thr Ser Glu Asp Leu Arg Ser Trp
545                 550                 555                 560

Leu Ser Asn Asn Val Arg Ser Asp Trp His Pro Val Gly Thr Cys Ala
            565                 570                 575

Met Leu Pro Lys Glu Leu Gly Gly Val Val Ser Pro Ala Leu Met Val
        580                 585                 590

Tyr Gly Thr Ser Asn Leu Arg Val Val Asp Ala Ser Ile Met Pro Leu
    595                 600                 605

Glu Val Ser Ser His Leu Met Gln Pro Thr Tyr Gly Ile Ala Glu Lys
        610                 615                 620

Ala Ala Asp Ile Ile Lys Asn Phe Tyr Lys Thr Gln His Lys Asn Gln
625                 630                 635                 640

Asn

<210> SEQ ID NO 4
<211> LENGTH: 1926
<212> TYPE: DNA
<213> ORGANISM: Mucor prainii

<400> SEQUENCE: 4
atgaagatca cagctgccat tatcactgtt gccacagcat ttgcttcttt tgcttctgct    60
caacaagaca caaattcttc ctcaactgat acttatgatt atgttatcgt tggcggcggt   120
gtagctggtt tggctttggc tagtcgtatc tctgaaaaca aggatgtcac tgttgctgtt   180
ctcgagtccg gtcctaatgc caatgataga tttgttgttt atgctcctgg catgtatggc   240
caagctgttg gcactgatct ctgtcctctc attcctacta ctcctcaaga aaatatgggc   300
aacagaagtc tcacaatcgc tactggtaga ttgctcggtg gtggcagtgc tattaatggt   360 ctcgttttgga cccgtggtgg cttgaaggat tacgatgctt gggaggagct cggtaaccct   420
ggatggaacg tgccaacttt gttcaagtac tttaagaagg tcgaaaactt cactcctcct   480
actcctgccc aaattgaata cggcgctact tatcagaaaa gtgctcatgg caagaaggga   540
cctattgatg tctctttcac gaactacgag ttctctcaat ctgctagctg aaacgcctca   600
ctcgaaaccc ttgatttcac tgcacttcct gatatcttga acggtacttt ggccggttac   660

```
tctaccactc ccaacatttt ggaccctgag actgttcaac gtgttgattc ctatactggt    720
tacattgctc cttacactag ccgtaacaac ctcaatgttt tggccaacca taccgtctcc    780
cgcattcaat ttgctcccaa gaatggtagc gaacctctca aggctaccgg tgttgaatgg    840
tatcccactg gcaacaagaa tcaaaagcaa attatcaagg cccgttatga agttatcatc    900
tcatctggtg ccattggtag tcctaagctt ttggaaatct ctggtatcgg taataaggat    960
atcgtctctg ctgctggtgt cgagtccttg attgacttgc ctggcgttgg ttccaacatg   1020
caagatcacg ttcatgctat cactgtctct actaccaata ttactggcta tactaccaac   1080
agcgtctttg tcaatgaaac ccttgcccaa gaacaaagag aagaatatga agccaacaag   1140
actggtatct gggctactac tcccaacaac ctcggttatc ctacgcccga acaactcttc   1200
aatggcaccg aattcgtttc tggaaaggag tttgctgaca agattcgtaa ctatactgat   1260
gaatgggcca actattatgc ttccaccaac gcctccaatg tcgagttatt aaagaagcaa   1320
tatgctattg tcgcctctcg ttacgaagag aactacttgt ctcctattga aatcaacttc   1380
actcctggtt atgagggtag cggtaatgtc gatttgcaaa acaacaagta ccaaactgtc   1440
aaccatgtct tgattgctcc tttaagtcgt ggttatactc acattaactc ttctgatgtg   1500
gaggatcatt ctgtcattaa tccccaatac tagtcgtatc ctatggatat tgatgtccat   1560
atcgcttcca ctaaacttgc tcgcgaaatc atcactgcct ctcccggtct tggtgacatt   1620
aacagtggcg aaatcgaacc cggtatgaat attacttctg aagacgacct tagatcttgg   1680
ttgagtaata atgtccgttc tgactggcat cctgttggta cttgtgctat gcttcccaag   1740
gaattaggtg gtgttgtcag ccccgctctc atggtttacg gcacttccaa cttgcgtgtt   1800
gttgatgctt cgattatgcc cctcgaagtc tcttctcatt tgatgcaacc cacctacggt   1860
attgctgaga aggctgctga cattattaag aatttctaca agactcaaca caagaaccaa   1920
aattag                                                              1926

<210> SEQ ID NO 5
<211> LENGTH: 14
<212> TYPE: PRT
<213> ORGANISM: Mucor prainii

<400> SEQUENCE: 5

Leu Val Glu Asn Phe Thr Pro Pro Thr Pro Ala Gln Ile Glu
1               5                   10

<210> SEQ ID NO 6
<211> LENGTH: 12
<212> TYPE: PRT
<213> ORGANISM: Mucor prainii

<400> SEQUENCE: 6

Ile Arg Asn Ser Thr Asp Glu Trp Ala Asn Tyr Tyr
1               5                   10

<210> SEQ ID NO 7
<211> LENGTH: 21
<212> TYPE: DNA
<213> ORGANISM: Artificial
<220> FEATURE:
<223> OTHER INFORMATION: primer 1 (forward)

<400> SEQUENCE: 7
cchachcchg chcaratyga r                                               21
```

```
<210> SEQ ID NO 8
<211> LENGTH: 24
<212> TYPE: DNA
<213> ORGANISM: Artificial
<220> FEATURE:
<223> OTHER INFORMATION: primer 2 (reverse)

<400> SEQUENCE: 8
rtartarttd gcccaytcrt cdgt                                          24

<210> SEQ ID NO 9
<211> LENGTH: 24
<212> TYPE: DNA
<213> ORGANISM: Artificial
<220> FEATURE:
<223> OTHER INFORMATION: primer 3 for 3'-RACE

<400> SEQUENCE: 9
cctacacctg cacaaattga atac                                          24

<210> SEQ ID NO 10
<211> LENGTH: 14
<212> TYPE: DNA
<213> ORGANISM: Artificial
<220> FEATURE:
<223> OTHER INFORMATION: primer 4 for 5'-RACE

<400> SEQUENCE: 10
ggcgttccag ctag                                                     14

<210> SEQ ID NO 11
<211> LENGTH: 20
<212> TYPE: DNA
<213> ORGANISM: Artificial
<220> FEATURE:
<223> OTHER INFORMATION: primer 5 for 5'-RACE

<400> SEQUENCE: 11
caagaaggga cctattgatg                                               20

<210> SEQ ID NO 12
<211> LENGTH: 22
<212> TYPE: DNA
<213> ORGANISM: Artificial
<220> FEATURE:
<223> OTHER INFORMATION: primer 6 for 5'-RACE

<400> SEQUENCE: 12
gagcactttt ctgataagta gc                                            22

<210> SEQ ID NO 13
<211> LENGTH: 22
<212> TYPE: DNA
<213> ORGANISM: Artificial
<220> FEATURE:
<223> OTHER INFORMATION: primer 7 for 5'-RACE

<400> SEQUENCE: 13
cgaactacga gttctctcaa tc                                            22

<210> SEQ ID NO 14
<211> LENGTH: 21
<212> TYPE: DNA
<213> ORGANISM: Artificial
<220> FEATURE:
<223> OTHER INFORMATION: primer 8 for 5'-RACE

<400> SEQUENCE: 14
```

```
cgtattcaat ttgtgcaggt g                                          21

<210> SEQ ID NO 15
<211> LENGTH: 18
<212> TYPE: DNA
<213> ORGANISM: Artificial
<220> FEATURE:
<223> OTHER INFORMATION: primer 9 (forward)

<400> SEQUENCE: 15
atgaagatca cagctgcc                                              18

<210> SEQ ID NO 16
<211> LENGTH: 18
<212> TYPE: DNA
<213> ORGANISM: Artificial
<220> FEATURE:
<223> OTHER INFORMATION: primer 10 (reverse)

<400> SEQUENCE: 16
ctaattttgg ttcttgtg                                              18
```